(12) United States Patent
Wang et al.

(10) Patent No.: US 10,695,299 B2
(45) Date of Patent: Jun. 30, 2020

(54) DISULFIRAM FORMULATION

(71) Applicant: UNIVERSITY OF WOLVERHAMPTON, Wolverhampton (GB)

(72) Inventors: Weiguang Wang, Wolverhampton (GB); Zhipeng Wang, Xi'an (CN); Xiu-Wu Bian, Chonqing (CN)

( * ) Notice: Subject to any disclaimer, the term of this patent is extended or adjusted under 35 U.S.C. 154(b) by 0 days.

(21) Appl. No.: 15/772,713

(22) PCT Filed: Nov. 7, 2016

(86) PCT No.: PCT/GB2016/053464
§ 371 (c)(1),
(2) Date: May 1, 2018

(87) PCT Pub. No.: WO2017/077336
PCT Pub. Date: May 11, 2017

(65) Prior Publication Data
US 2018/0311178 A1 Nov. 1, 2018

(30) Foreign Application Priority Data
Nov. 6, 2015 (GB) .................................. 1519643.9

(51) Int. Cl.
| | |
|---|---|
| *A61K 9/19* | (2006.01) |
| *A61P 35/00* | (2006.01) |
| *A61K 9/51* | (2006.01) |
| *A61K 31/145* | (2006.01) |
| *A61K 9/00* | (2006.01) |

(Continued)

(52) U.S. Cl.
CPC .......... *A61K 9/5153* (2013.01); *A61K 9/0019* (2013.01); *A61K 9/5192* (2013.01); *A61K 31/145* (2013.01); *A61K 31/44* (2013.01); *A61K 45/06* (2013.01); *A61P 35/00* (2018.01); *A61K 9/19* (2013.01)

(58) Field of Classification Search
CPC ...... A61K 31/145; A61K 31/44; A61K 45/06; A61K 9/0019; A61K 9/19; A61K 9/5153; A61K 9/5192; A61P 35/00
See application file for complete search history.

(56) References Cited

U.S. PATENT DOCUMENTS

| | | | |
|---|---|---|---|
| 6,288,110 B1* | 9/2001 | Marikovsky ........... | A61K 31/27 514/483 |
| 2010/0196436 A1* | 8/2010 | Gooberman ......... | A61K 9/0024 424/423 |
| 2014/0037715 A1 | 2/2014 | Wang | |

(Continued)

FOREIGN PATENT DOCUMENTS

| | | |
|---|---|---|
| CN | 102274347 A | 12/2011 |
| CN | 102357100 A | 2/2012 |

(Continued)

OTHER PUBLICATIONS

Makadia et al. (Polymers (Basel) 2011;13(3):1377-1397) (Year: 2011).*

(Continued)

*Primary Examiner* — Ernst V Arnold
(74) *Attorney, Agent, or Firm* — Clark & Elbing LLP

(57) ABSTRACT

Polymeric nanoparticles comprising disulfiram or derivatives thereof, and their use in the treatment of cancer.

22 Claims, 21 Drawing Sheets

Figure 1D:
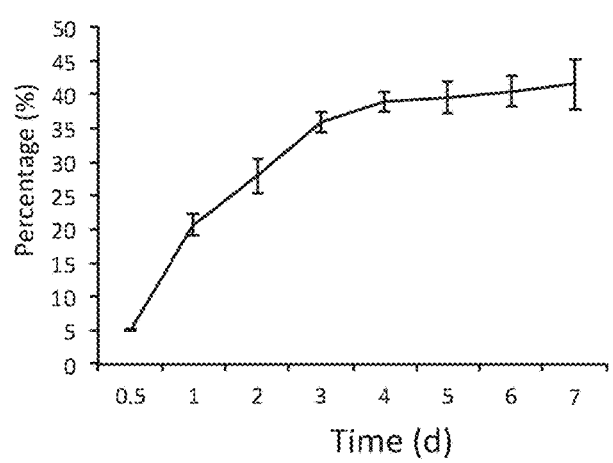

(51) Int. Cl.
*A61K 31/44* (2006.01)
*A61K 45/06* (2006.01)

(56) References Cited

U.S. PATENT DOCUMENTS

| | | | |
|---|---|---|---|
| 2018/0311178 A1 | 11/2018 | Wang et al. | |
| 2019/0117595 A1 | 4/2019 | Wang et al. | |

FOREIGN PATENT DOCUMENTS

| | | | |
|---|---|---|---|
| CN | 103221040 A | 7/2013 | |
| CN | 105125495 A | 12/2015 | |
| CN | 106377496 A | 2/2017 | |
| WO | WO-2008/068746 A2 | 6/2008 | |
| WO | WO-2015/120254 A1 | 8/2015 | |
| WO | WO-2017177947 A1 | 10/2017 | |

OTHER PUBLICATIONS

Panyam et al. (Journal of Pharmaceutical Sciences, 2004;93(7):1804-1814). (Year: 2004).*
Mutha et al. (Asian Journal of Pharmaceutics Oct.-Dec. 2009: pp. 266-273) (Year: 2009).*
Skrott et al.(Nature Dec. 2017;552:23 pages). (Year: 2017).*
Chun, C. What are the most curable cancers? [online] retrieved on Jul. 19, 2019 from: https://www.medicalnewstoday.com/articles/322700.php; 4 pages). (Year: 2019).*
Hoda et al., "Influence of stabilizers on the production of disulfiram-loaded poly(lactic-co-glycolic acid) nanoparticles and their anticancer potential," Ther Deliv. 6(1):17-25 (2015).
Fasehee et al., "The inhibitory effect of disulfiram encapsulated PLGA NPs on tumor growth: Different administration routes," Mater Sci Eng C Mater Bio Appl. 63:587-95 (2016).
Hoda et al., "Anti-proliferative and apoptosis-triggering potential of disulfiram and disulfiram-loaded polysorbate 80-stabilized PLGA nanoparticles on hepatocellular carcinoma Hep3B cell line," Nanomedicine. 12(6):1641-50 (2016).
Ketola et al., "Chemical Biology Drug Sensitivity Screen Identifies Sunitinib as Synergistic Agent with Disulfiram in Prostate Cancer Cells," PLoS One. 7(12):e51470 (2012) (11 pages).
Löbler et al., "Drug delivery by nanoparticles—facing the obstacles," IFMBE Proceedings. 22:2335-2338 (2009).
Phillips et al., "Sustained-release characteristics of a new implantable formulation of disulfiram," J Pharm Sci. 73(12):1718-20 (1984).
Song et al., "Stable loading and delivery of disulfiram with mPEG-PLGA/PCL mixed nanoparticles for tumor therapy," Nanomedicine. 12(2):377-86 (2016).
Cheriyan et al. "Disulfiram suppresses growth of the malignant pleural mesothelioma cells in part by inducing apoptosis," PLoS One. 9(4):e93711 (2014) (14 pages).
International Search Report and Translation for International Patent Application No. PCT/CN2017/080463, dated Jul. 14, 2017 (9 pages).
Faiman et al., "Disulfiram distribution and elimination in the rat after oral and intraperitoneal administration," Alcohol Clin Exp Res. 4(4):412-9 (1980).

* cited by examiner

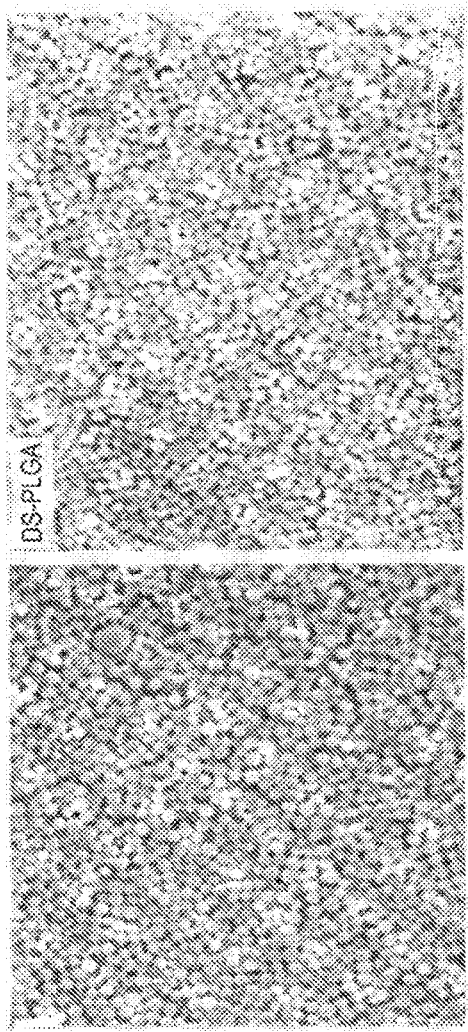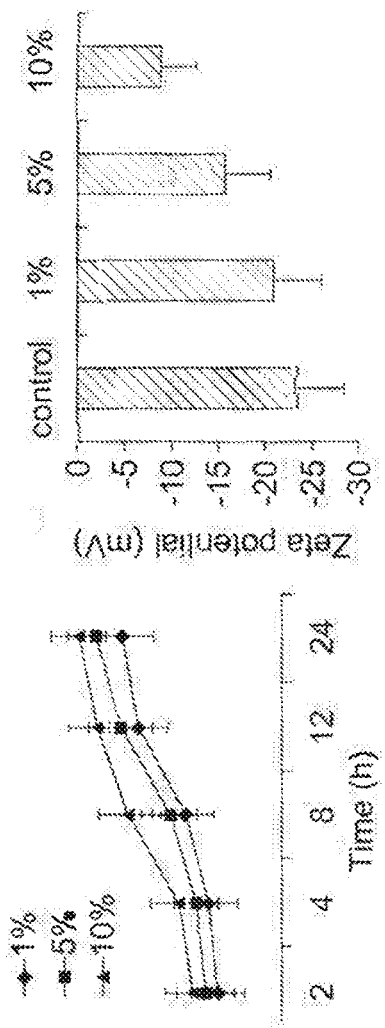
FIG. 1A
FIG. 1B
FIG. 1C x400

FIG. 9A
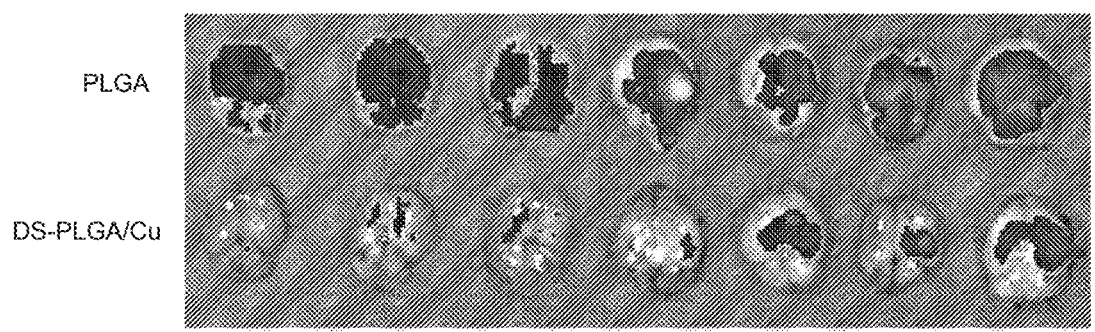
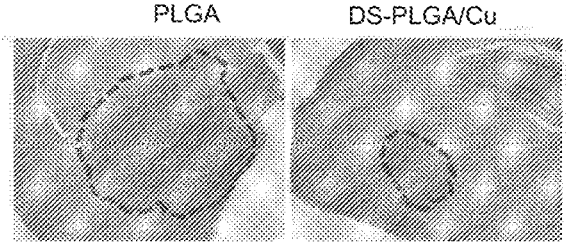
FIG. 9B

DISULFIRAM FORMULATION

The invention relates to polymeric nanoparticles comprising disulfiram or derivatives thereof and uses thereof, in particular the use of such particles for the treatment of cancer.

Disulfiram, a commercialised anti-alcoholism drug, has been demonstrated to be a potential anticancer agent with strong cancer cell toxicity but with very limited toxicity to vital organs in vivo. In addition, disulfiram has been shown to eradicate breast cancer and glioblastoma stem cells. However, the translation of disulfiram into clinical cancer treatment is severely limited by its short half-life in the bloodstream. Therefore there is a need to develop more stable, clinically applicable disulfiram formulations which demonstrate an extended half-life in vivo.

According to a first aspect of the invention, there is provided a nanoparticle comprising disulfiram or a derivative thereof encapsulated by the copolymer poly(lactic-co-glycolic acid) (PLGA) or polylactic acid (PLA).

According to a second aspect of the invention, there is provided a nanoparticle composition comprising one or more nanoparticles comprising disulfiram or a derivative thereof wherein the disulfiram or a derivative thereof is encapsulated by the copolymer poly(lactic-co-glycolic acid) (PLGA) or polylactic acid (PLA).

According to a third aspect of the invention, there is provided a pharmaceutical composition comprising one or more nanoparticles comprising disulfiram or a derivative thereof wherein the disulfiram or a derivative thereof is encapsulated by the copolymer poly(lactic-co-glycolic acid) (PLGA) or polylactic acid (PLA); and a pharmaceutically acceptable carrier.

A 'nanoparticle' refers to any particle having a diameter of less than 1000 nm e.g. about 10 nm to 300 nm. For example, the nanoparticle can have a diameter of less than about 300 nm, less than about 200 nm, less than about 150 nm, less than about 100 nm, less than about 50 nm, less than about 30 nm, less than about 10 nm, or less than about 3 nm. In particular embodiments, the nanoparticle of the present invention has a diameter of about 60 nm to about 120 nm, about 60 nm to about 140 nm, about 60 nm to about 150 nm, about 70 nm to about 120 nm, about 70 to about 130 nm or 80 nm to about 200 nm or about 100 nm to about 200 nm.

Disulfiram has the chemical formula:

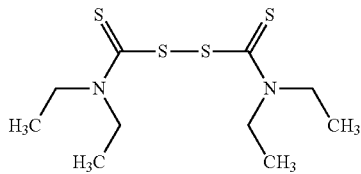 [SMILES: CCN(CC)C(=S)SSC(=S)N(CC)CC]

A derivative of disulfiram may include diethyldithiocarbamic acid or diethyldithiocarbonate (DDC) or a metabolite thereof, or a metabolite of disulfiram. Preferably the derivative does not comprise copper.

The nanoparticle of the invention may include about 0.2 to about 35 weight percent, about 3 to about 40 weight percent, about 1 to about 30 weight percent, about 5 to about 30 weight percent, about 10 to about 30 weight percent, about 15 to about 25 weight percent, or even about 4 to about 25 weight percent of disulfiram or a derivative thereof.

In an embodiment, disulfiram or a derivative thereof may or may not be conjugated (e.g. covalently bound e.g. directly or through a linking moiety) to PLGA or polylactic acid (PLA), or a PLGA portion of a copolymer such as PLGA-PEG.

'PLGA' as used herein refers to a biocompatible and biodegradable co-polymer of lactic acid and glycolic acid, and various forms of PLGA can be characterised by the ratio of lactic acid:glycolic acid. Lactic acid may be L-lactic acid, D-lactic acid, or D,L-lactic acid. The degradation of PLGA may be adjusted by altering the lactic acid-glycolic acid ratio. In some embodiments, PLGA to be used in accordance with the present invention can be characterised by a lactic acid:glycolic acid ratio of approximately 85:15, approximately 75:25, approximately 60:40, approximately 50:50, approximately 40:60, approximately 25:75, or approximately 15:85. Preferably, the lactic acid:glycolic acid ratio is approximately 50:50.

In some embodiments, the ratio of lactic acid to glycolic acid may be selected to optimize for various parameters such as water uptake, therapeutic agent (disulfiram or a derivative thereof) release and/or polymer degradation kinetics can be optimised.

'PLA' as used herein refers to a biocompatible and biodegradable polymer of lactic acid.

The nanoparticle of the invention may include about 10 to about 99 weight %, or about 20 to about 80 weight %, about 40 to about 80 weight %, or about 30 to about 50 weight %, or about 70 to 90 weight % of PLGA.

PLGA may have a number average molecular weight of about 5 to about 15 kDa, or about 5 to about 12 kDa. Preferably, PLGA may have a number average molecular weight of about 8 to about 12 kDa.

In some embodiments, PLGA and disulfiram or a derivative thereof to be used in accordance with the present invention can be characterised by a PLGA:disulfiram or derivative thereof ratio of approximately 4:1, 3:1, or 2:1 Preferably, the PLGA:disulfiram or derivative thereof ratio is approximately 2:1.

In some embodiments, nanoparticles of the invention may also include a fatty alcohol, which may increase the rate of drug release. For example, nanoparticles of the invention may include a $C_8$-$C_{30}$ alcohol such as cetyl alcohol, octanol, stearyl alcohol, arachidyl alcohol, docosonal, or octasonal.

The nanoparticle of the invention may be administered in combination with a tyrosine kinase inhibitor selected from afatinib, bosutinib, dasatinib, erlotinib, gefitinib, imatinib, nilotinib, pazopanib, ponatinib, regorafenib, semaxinib, sorafenib, sunitinib, telatinib or vandetanib. Preferably, the tyrosine kinase inhibitor is sorafenib.

In a particular embodiment, a nanoparticle composition of the invention comprises nanoparticles having a diameter of about 60 nm to about 150 nm. Such nanoparticles may include disulfiram or a derivative thereof of about 40 weight percent and about 60 weight percent of a PLGA copolymer.

In a preferred embodiment, the drug loading content of a nanoparticle is between about 10% and about 30%.

In a preferred embodiment, the drug loading content is about 27 mg of disulfiram/mg of PLGA.

In a preferred embodiment, the encapsulation efficiency of a nanoparticle is between about 68% and about 97%.

In a preferred embodiment, the invention provides a nanoparticle in which the only active ingredient encapsulated is disulfiram or a derivative thereof. Preferably the nanoparticle does not encapsulate copper.

Nanoparticles of the invention may have controlled release properties, e.g. may be capable of delivering an amount of active agent to a subject e.g. to a specific site in a subject and/or over an extended period of time, e.g. over 1 day, 1 week or more. In some embodiments, nanoparticles of the invention immediately release (e.g. over about 1 minute to about 30 minutes), less than about 2%, less than about 5%, or less than about 10% of disulfiram or a derivative thereof, for example when placed in a phosphate buffer solution at room temperature and/or 37° C.

Nanoparticles of the invention, may, in some embodiments, release disulfiram or a derivative thereof when placed in an aqueous solution, for example, at 25° C. with a rate substantially corresponding to a) from about 0.01 to about 20% of the total disulfiram or a derivative thereof is released after about 1 hour; b) from about 10 to about 50% of the total disulfiram or a derivative thereof is released after about 8 hours; c) from about 30 to about 50% of the total disulfiram or a derivative thereof is released after 12 hours; and d) not less than about 50% of the total disulfiram or a derivative thereof is released after about 24 hours.

Nanoparticles of the present invention may be combined with a pharmaceutical acceptable carrier to form a pharmaceutical composition, according to another aspect of the invention. As would be appreciated by one of skill in the art, the carriers may be chosen based on the route of administration as described below, the location of the target tissue, the time course of delivery of the drug, etc. Examples of carriers are described later.

The pharmaceutical compositions of this invention can be administered to a subject by any means known in the art including parenteral routes. The term "subject," as used herein, refers to humans as well as non-humans, including, for example, mammals, birds, reptiles, amphibians, and fish. For instance, the non-humans may be mammals (e.g., a rodent, a mouse, a rat, a rabbit, a monkey, a dog, a cat, a primate, or a pig). In certain embodiments parenteral routes are desirable since they avoid contact with the digestive enzymes that are found in the alimentary canal.

According to such embodiments, compositions of the invention may be administered by injection e.g., intravenous.

In a particular embodiment, the nanoparticles of the present invention are administered to a subject in need thereof systemically, e.g., by IV infusion or injection.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension, or emulsion in a nontoxic parenterally acceptable diluent or solvent, for example, as a solution in 1,3-butanediol. Among the acceptable vehicles and solvents that may be employed are water, Ringer's solution, U.S.P., and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables. In one embodiment, the inventive conjugate is suspended in a carrier fluid comprising 1% (w/v) sodium carboxymethyl cellulose and 0.1% (v/v) TWEEN™ 80. The injectable formulations can be sterilized, for example, by filtration through a bacteria-retaining filter, or by incorporating sterilizing agents in the form of sterile solid compositions which can be dissolved or dispersed in sterile water or other sterile injectable medium prior to use.

In some embodiments, a composition suitable for freezing is contemplated, including nanoparticles disclosed herein and a solution suitable for freezing, e.g. a sucrose and/or cyclodextrin solution is added to the nanoparticle suspension. The sucrose may e.g., as a cryoprotectant to prevent the particles from aggregating upon freezing. For example, provided herein is a nanoparticle formulation comprising a plurality of disclosed nanoparticles, sucrose and water.

Methods of the invention may include the administration of a nanoparticle composition or a pharmaceutical composition of the invention, wherein the composition is administered over a period of three weeks, a month, or two months or more. For example, disclosed herein are methods of treating cancers that include administering a nanoparticle composition or a pharmaceutical composition of the invention over a period of at least two weeks, three weeks, one month or administered over a period of about 2 weeks to about 6 months or more, wherein the interval between each administration is no more than about once a day, once a week, once every two weeks, once every three weeks, or once every month, and wherein the dose of disulfiram or a derivative thereof at each administration is about, preferably at between about 1 mg/kilo and about 20 mg/kilo, more preferably at about 10 mg/kilo.

The invention provides a method for treating or preventing cancer, the method comprising administering to a subject in need thereof a therapeutically effective amount of a nanoparticle composition or a pharmaceutical composition of the invention. By analogy, it is also within the scope of the invention to use the nanoparticle composition or pharmaceutical composition of the invention in the manufacture of a medicament for the treatment of cancer. Similarly, by analogy, the invention also provides a nanoparticle composition or a pharmaceutical composition of the invention for use in the treatment of cancer.

In some embodiments, nanoparticles in accordance with the present invention may be used to treat, alleviate, ameliorate, relieve, delay onset of, inhibit progression of, reduce severity of, and/or reduce incidence of one or more symptoms or features of cancer.

According to another aspect of the invention, there is provided a method of treating cancer in a subject in need thereof, comprising administering to the subject a therapeutically effective amount of a nanoparticle composition or a pharmaceutical composition comprising nanoparticles disulfiram or a derivative thereof encapsulated by the copolymer poly(lactic-co-glycolic acid) (PLGA) or PLA.

According to another aspect of the invention, there is provided a nanoparticle, a nanoparticle composition or pharmaceutical composition according to the invention for use in treating cancer in a subject in need thereof.

According to a further aspect the invention provides the use of a nanoparticle, nanoparticle composition or a pharmaceutical composition according to the invention in the manufacture of a medicament for the treatment of cancer.

The cancer can be any suitable cancer, for example, renal cancer, bladder cancer, ovarian cancer, breast cancer, endometrial cancer, pancreatic cancer, lymphoma, thyroid cancer, bone cancer, CNS cancer, leukaemia, liver cancer, prostrate cancer, lung cancer, colon cancer, rectal cancer, brain cancer or melanoma. Preferably, the cancer is liver cancer. More preferably, the cancer is brain cancer.

It will be appreciated that the term "treatment" and "treating" as used herein means the management and care of a subject for the purpose of combating a condition, such as a disease or a disorder. The term is intended to include the full spectrum of treatments for a given condition from which the subject is suffering, such as administration of the nanoparticles to alleviate the symptoms or complications, to delay the progression of the disease, disorder or condition, to alleviate or relief the symptoms and complications, and/or to cure or eliminate the disease, disorder or condition as well as to prevent the condition, wherein prevention is to be understood as the management and care of a subject for the purpose of combating the disease, condition, or disorder and includes the administration of the nanoparticles to prevent the onset of the symptoms or complications. The subject to be treated is preferably a mammal, in particular a human being, but it may also include animals, such as dogs, cats, horses, cows, sheep and pigs.

Many diseases are treated using more than one medicament in the treatment, either concomitantly administered or sequentially administered. It is therefore within the scope of the invention to use a nanoparticle composition or a pharmaceutical composition of the invention in a therapeutic method for the treatment of cancer as an adjunct to, or in conjunction with, other established therapies normally used in the treatment of the cancer. By analogy, it is also within the scope of the invention to use a nanoparticle composition or a pharmaceutical composition of the invention in combination with other therapeutically active compounds normally used in the treatment of cancer in the manufacture of a medicament for the treatment of cancer. Furthermore, by analogy, the invention also provides a nanoparticle composition or a pharmaceutical composition according to the invention in combination with other therapeutically active compounds normally used in the treatment of cancer, for use in the treatment of cancer.

In one embodiment a nanoparticle composition or a pharmaceutical composition of the invention may be for use in combination with surgery or radiotherapy or chemotherapy. The chemotherapeutic agent may be one or more of a Gliadel® Wafer (carmustine), 5-fluorouracil, doxorubicin, paclitaxel and gemcitabine. Preferably this combination is used in the treatment of one or more of colon cancer, breast cancer, liver cancer and glioblastoma (brain cancer). All the aforementioned examples show a very strong synergistic effect.

The combination treatment may be carried out in any way deemed necessary or convenient by the person skilled in the art and for the purpose of this specification, no limitations with regard to the order, amount, repetition or relative amount of the compounds to be used in combination is contemplated.

In the present context, the term "pharmaceutically acceptable salt" is intended to indicate salts which are not harmful to a patient. Such salts include pharmaceutically acceptable acid addition salts, pharmaceutically acceptable metal salts, ammonium and alkylated ammonium salts. Acid addition salts include salts of inorganic acids as well as organic acids. Representative examples of suitable inorganic acids include hydrochloric, hydrobromic, hydroiodic, phosphoric, sulfuric, nitric acids and the like. Representative examples of suitable organic acids include formic, acetic, trichloroacetic, trifluoroacetic, propionic, benzoic, cinnamic, citric, fumaric, glycolic, lactic, maleic, malic, malonic, mandelic, oxalic, picric, pyruvic, salicylic, succinic, methanesulfonic, ethanesulfonic, tartaric, ascorbic, pamoic, bismethylene salicylic, ethanedisulfonic, gluconic, citraconic, aspartic, stearic, palmitic, EDTA, glycolic, p-aminobenzoic, glutamic, benzenesulfonic, p-toluenesulfonic acids and the like. Further examples of pharmaceutically acceptable inorganic or organic acid addition salts include the pharmaceutically acceptable salts listed in J. Pharm. Sci. 1977, volume 66, issue 2. Examples of metal salts include lithium, sodium, potassium, magnesium salts and the like. Examples of ammonium and alkylated ammonium salts include ammonium, methylammonium, dimethylammonium, trimethylammonium, ethylammonium, hydroxyethylammonium, diethylammonium, butylammonium, tetramethylammonium salts and the like.

The pharmaceutical compositions according to the invention may be formulated with pharmaceutically acceptable carriers or diluents as well as any other known adjuvants and excipients in accordance with conventional techniques such as those disclosed in Remington: The Science and Practice of Pharmacy, 19th Edition, Gennaro, Ed., Mack Publishing Co., Easton, Pa., 1995.

Suitable pharmaceutical carriers include inert solid diluents or fillers, sterile aqueous solutions and various organic solvents. Examples of solid carriers are lactose, terra alba, sucrose, cyclodextrin, talc, gelatine, agar, pectin, acacia, magnesium stearate, stearic acid and lower alkyl ethers of cellulose. Examples of liquid carriers are syrup, peanut oil, olive oil, phospholipids, fatty acids, fatty acid amines, polyoxyethylene and water. In addition, the compounds of the invention may form solvates with water or common organic solvents. Such solvates are also encompassed within the scope of the present invention.

The composition may further comprise a buffer system, preservative(s), tonicity agent(s), chelating agent(s), stabilizers and surfactants, which is well known to the skilled person. For convenience reference is made to Remington: The Science and Practice of Pharmacy, 20th edition, 2000. The composition may also further comprise one or more therapeutic agents active against the same disease state.

The composition may further comprise copper. In one embodiment, copper may be co-administered with the composition according to the invention.

Methods to produce controlled release systems useful for compositions of the current invention include, but are not limited to, crystallization, condensation, co-crystallization, precipitation, co-precipitation, emulsification, dispersion, high pressure homogenisation, en-capsulation, spray drying, microencapsulating, coacervation, phase separation, solvent evaporation to produce microspheres, extrusion and supercritical fluid processes. General reference is made to Handbook of Pharmaceutical Controlled Release (Wise, D. L., ed. Marcel Dekker, New York, 2000) and Drug and the Pharmaceutical Sciences vol. 99: Protein Composition and Delivery (MacNally, E. J., ed. Marcel Dekker, New York, 2000).

Pharmaceutical compositions for oral administration include solid dosage forms such as hard or soft capsules, tablets, troches, dragees, pills, lozenges, powders and granules and liquid dosage forms for oral administration include solutions, emulsions, aqueous or oily suspensions, syrups and elixirs, each containing a predetermined amount of the active ingredient, and which may include a suitable excipient.

Compositions intended for oral use may be prepared according to any known method, and such compositions may contain one or more agents selected from the group consisting of sweetening agents, flavouring agents, colouring agents, and preserving agents in order to provide pharmaceutically elegant and palatable preparations.

Parenteral administration may be performed by subcutaneous, intramuscular, intraperitoneal or intravenous injection by means of a syringe, optionally a pen-like syringe. Alternatively, parenteral administration can be performed by means of an infusion pump. A further option is a composition which may be a solution or suspension for the administration of the prolactin receptor antagonist in the form of a nasal or pulmonal spray. As a still further option, the pharmaceutical compositions containing the compound of the invention can also be adapted to transdermal administration, e.g. by needle-free injection or from a patch, optionally an iontophoretic patch, or transmucosal, e.g. buccal, administration.

Pharmaceutical compositions for parenteral administration include sterile aqueous and non-aqueous injectable solutions, dispersions, suspensions or emulsions as well as sterile powders to be reconstituted in sterile injectable solutions or dispersions prior to use.

The term "aqueous composition" is defined as a composition comprising at least 50% w/w water. Likewise, the term "aqueous solution" is defined as a solution comprising at least 50% w/w water, and the term "aqueous suspension" is defined as a suspension comprising at least 50% w/w water. Such aqueous solutions should be suitably buffered if necessary and the liquid diluent first rendered isotonic with sufficient saline or glucose. The aqueous solutions are particularly suitable for intravenous, intramuscular, subcutaneous and intraperitoneal administration. The sterile aqueous media employed are all readily available by standard techniques known to those skilled in the art. Depot injectable formulations are also contemplated as being within the scope of the present invention.

When the use of the invention is combined with a second therapeutic agent active against the same disease state, they may conveniently be administered alone or in combination, in either single or multiple doses, sequentially or simultaneously, by the same route of administration, or by a different route.

Generally, depending on the intended mode of administration, the nanoparticle composition or pharmaceutical composition will contain about 0.005% to 95%, preferably about 0.5% to 50%, by weight of a nanoparticle composition or pharmaceutical composition of the invention. The percentage of active compound e.g. disulfiram or a derivative thereof contained in the composition is dependent on the specific nature of the composition, as well as the activity of the compound and the needs of the subject. Percentages of active ingredient of 0.01% to 90% in solution are generally employable, whilst the amounts can be higher if the composition is a solid which will be subsequently diluted. In some embodiments, the composition will comprise from 1% to 50% of the active compound e.g. disulfiram or a derivative thereof in solution.

The use of a nanoparticle composition or a pharmaceutical composition according to the invention will generally be in an amount effective to achieve the intended result, for example in an amount effective to treat or prevent the particular disease being treated. The nanoparticle composition or pharmaceutical composition may be administered therapeutically to achieve therapeutic benefit. By therapeutic benefit is meant eradication or amelioration of the underlying disorder being treated and/or eradication and/or amelioration of one or more of the systems associated with the underlying disorder. Therapeutic benefit also includes halting or slowing the progression of the disease, regardless of whether improvement is realised.

The exact dosage will depend upon the frequency and mode of administration, the sex, age, weight and general condition of the subject treated, the nature and severity of the condition treated and any concomitant diseases to be treated and other factors evident to those skilled in the art. Determination of the effective dosage is well within the capabilities of those skilled in the art.

When a nanoparticle composition or pharmaceutical composition of the invention is used in combination with a second therapeutic agent active against the same disease state the dose of each compound may differ from that when the nanoparticle composition or pharmaceutical composition is used alone. Appropriate doses will be readily appreciated by those skilled in the art.

In one preferred embodiment, the nanoparticle composition or pharmaceutical composition will take the form of a unit dosage form. For example, the nanoparticle composition or pharmaceutical composition may be provided in a vial or other container. The vial or other container may contain the nanoparticle composition or pharmaceutical composition in the form of a liquid, a solid to be suspended, a dry powder, a lyophilisate, or any other suitable form.

It will be appreciated that optional features applicable to one aspect or embodiment of the invention can be used in any combination, and in any number. Moreover, they can also be used with any of the other aspects or embodiments of the invention in any combination and in any number. This includes, but is not limited to, the dependent claims from any claim being used as dependent claims for any other claim in the claims of this application.

The invention will be further described, by means of non-limiting example only, with reference to the following figures and experimental examples.

FIG. 1A-F—demonstrates in vitro characterisation of PLGA-disulfiram.

FIG. 1A—shows scanning electron micrographs of PLGA empty nanoparticles (Empty NPs) and PLGA encapsulated disulfiram nanoparticles (PLGA-DS NPs). Scale bars correspond to 1 μm.

FIG. 1B—demonstrates the influence of BSA concentration on the size of nanoparticles.

FIG. 1C—demonstrates the influence of BSA concentration on Zeta potential.

FIG. 1D—demonstrates in vitro release profiles of disulfiram. PLGA-disulfiram was incubated in PBS/0.5% Tween80 at 37° C. The concentration of disulfiram in the solution was measured at the indicated time points using HPLC.

Figure 1E:
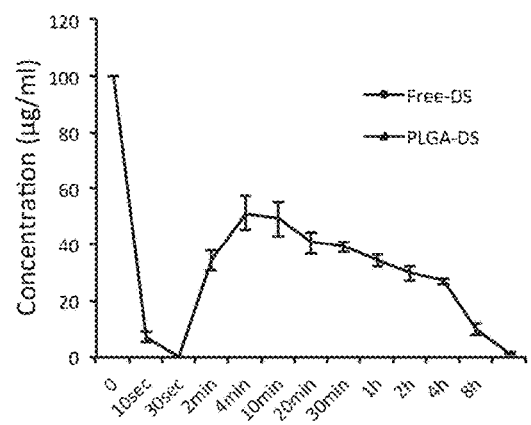

FIG. 1E—demonstrates in vitro half-life of disulfiram in horse serum. PLGA-disulfiram, and non-encapsulated free disulfiram were incubated in horse serum at 37° C. for indicated time lengths.

Figure 1F:
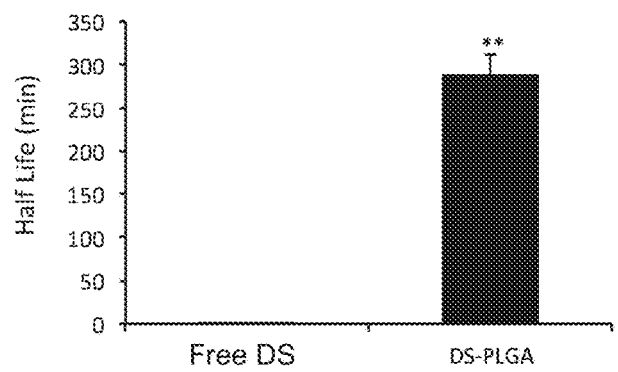

FIG. 1F—demonstrates in vitro half-life of free-, and PLGA-disulfiram in horse serum. To determine the half-life of disulfiram in vitro, the free disulfiram and disulfiram-PLGA were dispersed into horse serum (100 μg/ml) and incubated at 37° C. The free disulfiram was rapidly degraded in the serum to undetectable levels within 30 seconds which is even much shorter than previously published data (4 min).

Figure 2A:
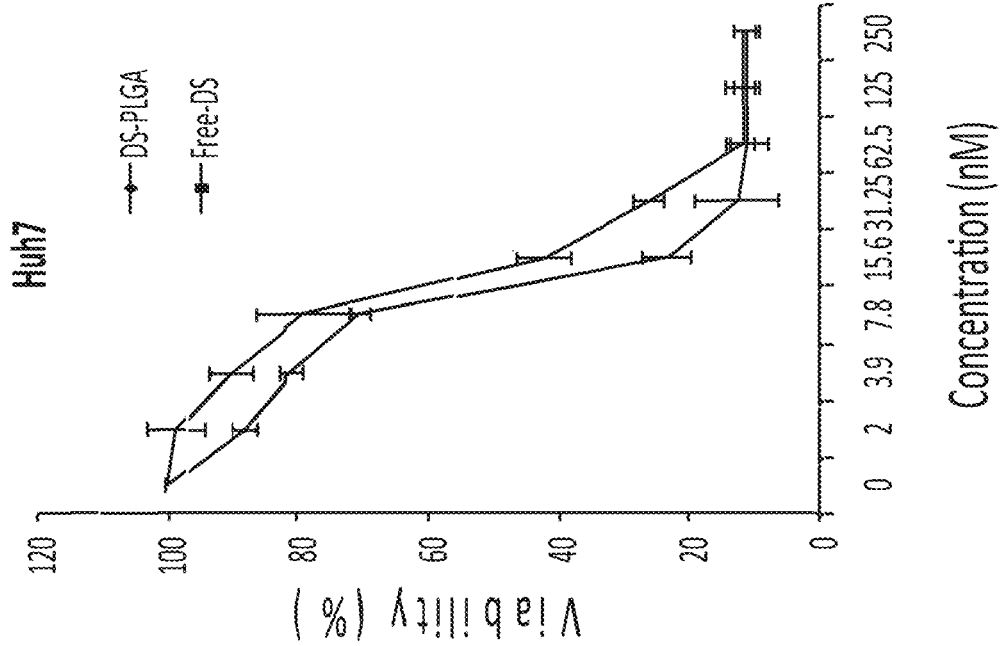

FIG. 2A—shows the results of an MTT cytotoxicity assay. The liver cancer cell line, PLC/PRF/5 was exposed to free Disulfiram and PLGA-Disulfiram for 72 h. n=3, the vertical bars represent SD.

Figure 2B:
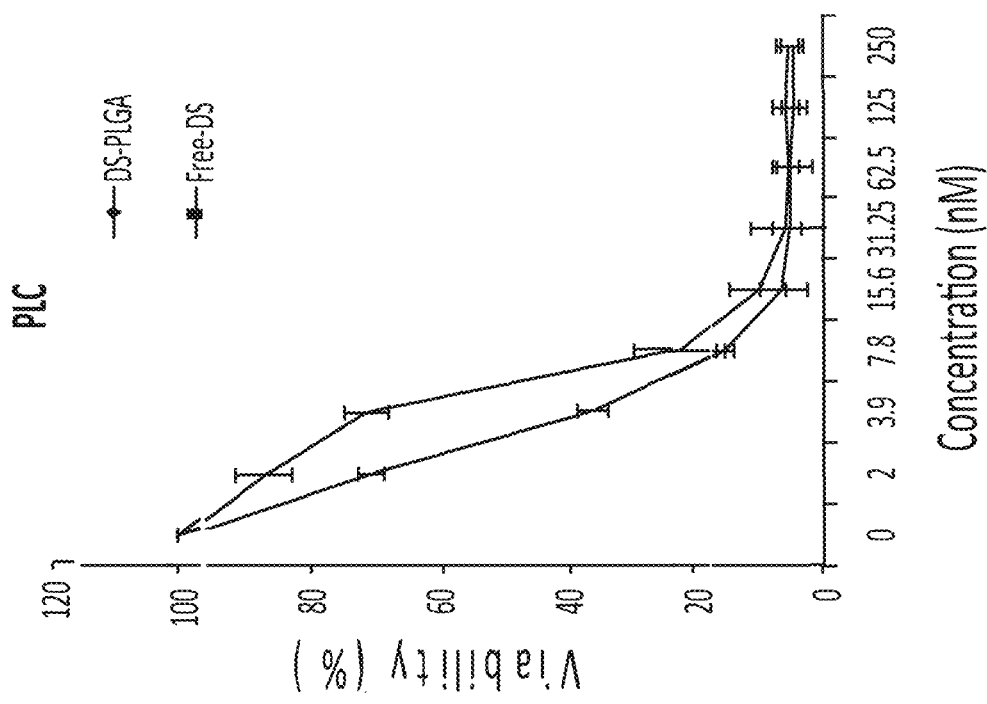

FIG. 2B—shows the results of an MTT cytotoxicity assay. The liver cancer cell line, Huh7 was exposed to free Disulfiram and PLGA-Disulfiram for 72 h. n=3, the vertical bars represent SD.

Figure 3B:
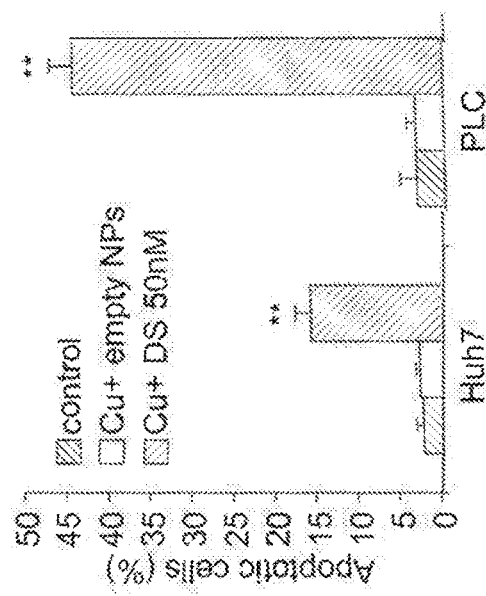
Figure 3A:
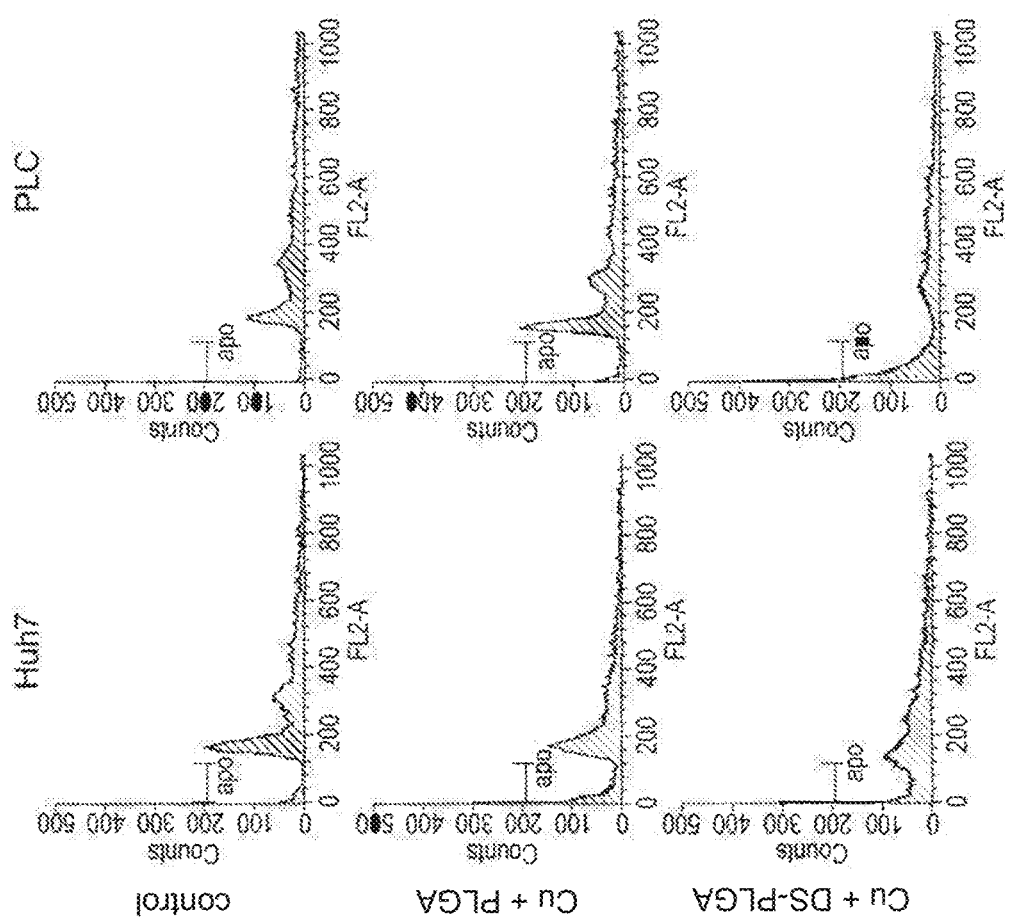

FIG. 3A-B—shows PLGA-disulfiram induced apoptosis in liver cancer cell lines. PLC/PRF/5 and Huh7 cell lines were exposed to empty PLGA nanoparticles plus $CuCl_2$ (5 μM), or PLGA-disulfiram nanoparticles (50 nM) plus $CuCl_2$ (5 μM) for 4 h. DNA content was measured by flow cytometry analysis.

FIG. 3A—shows a comparison of sub-G1 (apoptotic) population in different treated groups. After exposure to Disulfiram-PLGA (50 nM) and $CuCl_2$ (5 μM) for 4 hours, the apoptotic cells (sub-G1 population) were identified by DNA content assay using flow cytometry analysis.

FIG. 3B—Statistic analysis of FIG. 3A. The column represents mean of three measurements and the vertical bar represents SD. ** p<0.01.

FIG. 4A-E—shows PLGA-disulfiram nanoparticles inhibit cancer stem cell marker expression in liver cancer cell lines. PLC and Huh7 cells were cultured in either normoxic or hypoxic condition for 5 days. Then hypoxic cells were treated with empty PLGA nanoparticles plus $CuCl_2$ (5 µM), or PLGA-disulfiram nanoparticles (20 nM) plus $CuCl_2$ (5 µM) for 24 h ALDH activity and expression of CD133 were measured by flow cytometry using ALDE-FLUOR kit and CD133 antibody. After 72 hr exposure, the cytotoxicity of 5-FU and Sorafenib was determined in the normoxically and hypoxically cultured HCC cell lines.

Figure 4B:
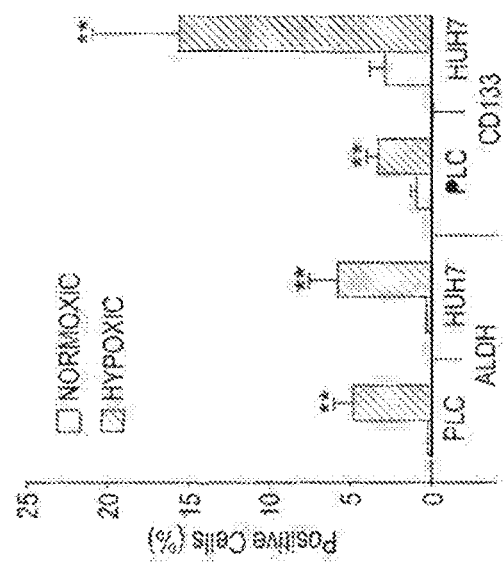
Figure 4A:
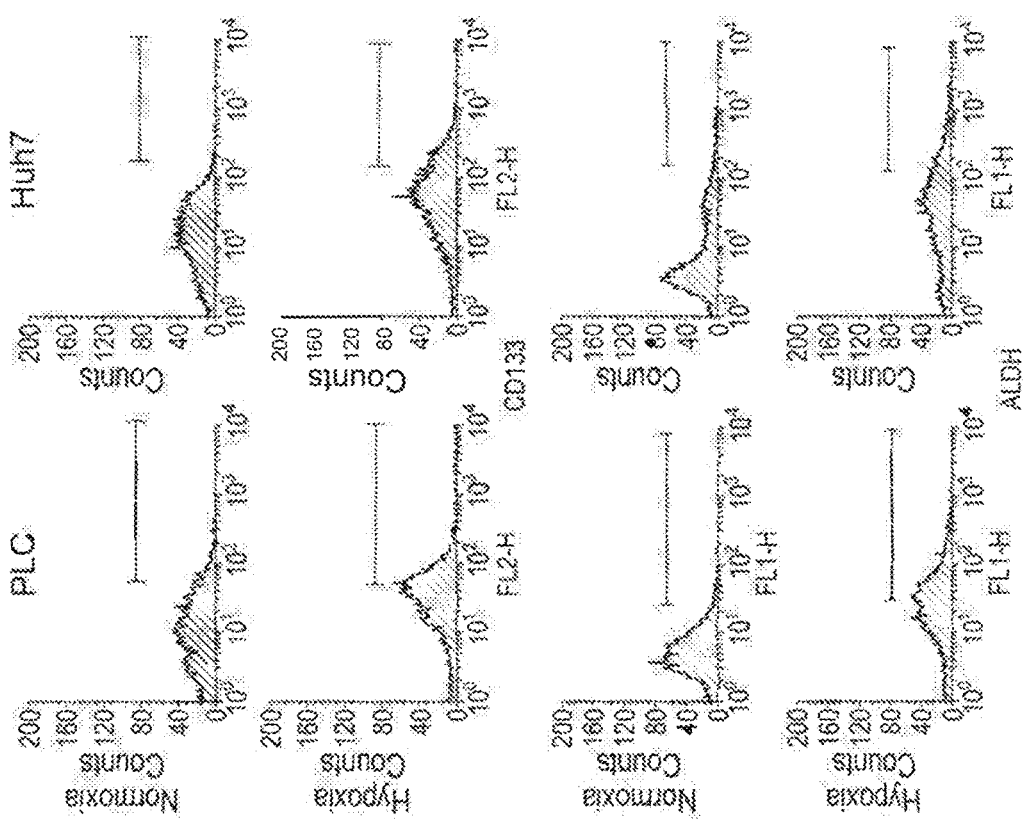

FIG. 4A—shows dot plots which represent ALDH activity in different groups.

FIG. 4B—shows the percentage of ALDH positive cells in PLGA-disulfiram nanoparticles treated and control groups.

Figure 4D:
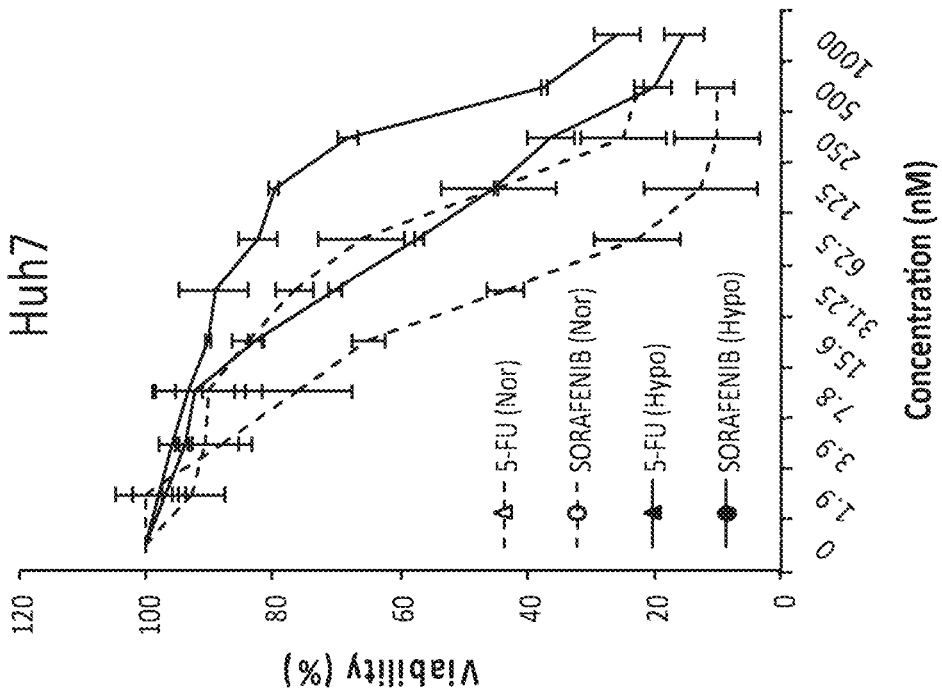
Figure 4C:
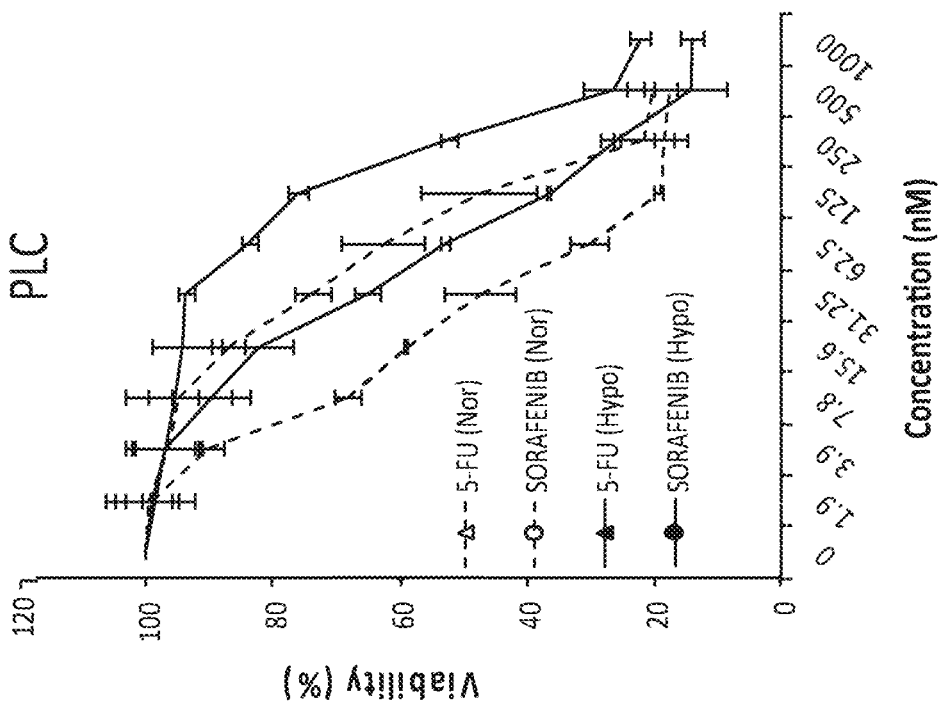

FIG. 4C—shows dot plots which represent CD133 positive cells in different groups.

FIG. 4D—shows the percentage of CD133 positive cells in PLGA-disulfiram nanoparticles treated and control groups.

Figure 4E:
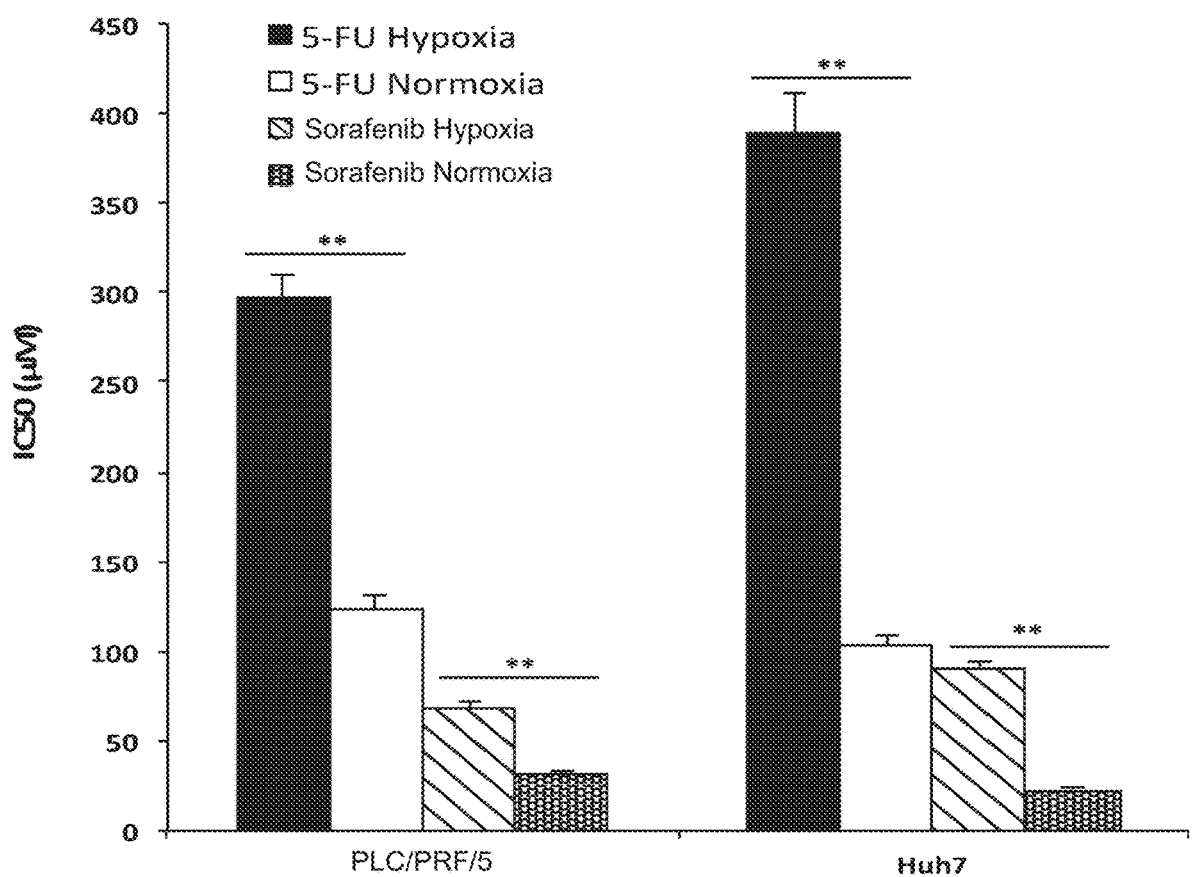

FIG. 4E—shows hypoxiainduced chemoresistance of HCC cells to 5-FU and Sorafenib. After 72 h exposure, the cytotoxicity of 5-FU and Sorafenib was determined in the normoxically and hypoxically cultured HCC cell lines.

FIG. 5A-D—shows PLGA-disulfiram nanoparticles inhibited CSC markers and eradicated clonogenicity in HCC cell lines.

Figure 6A:
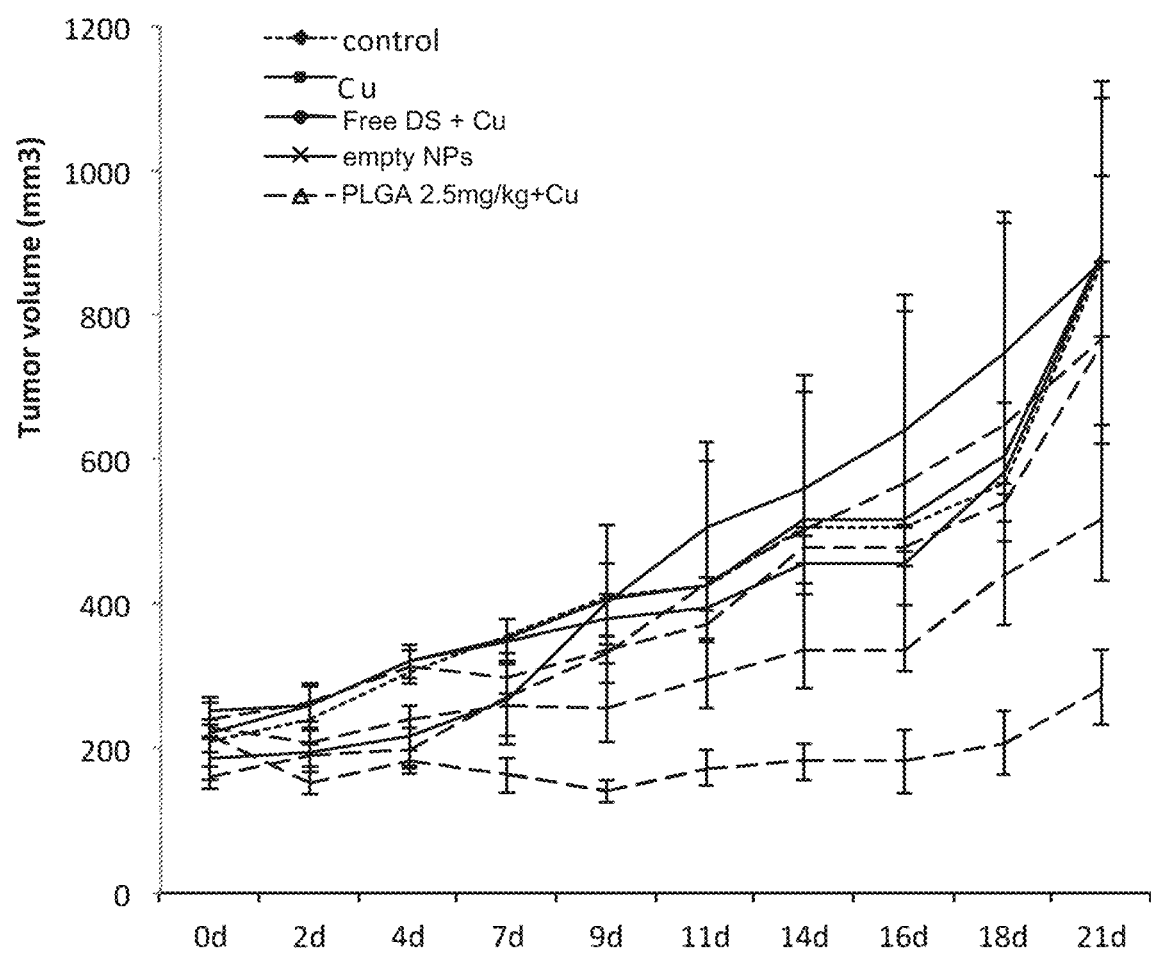
Figure 6B:
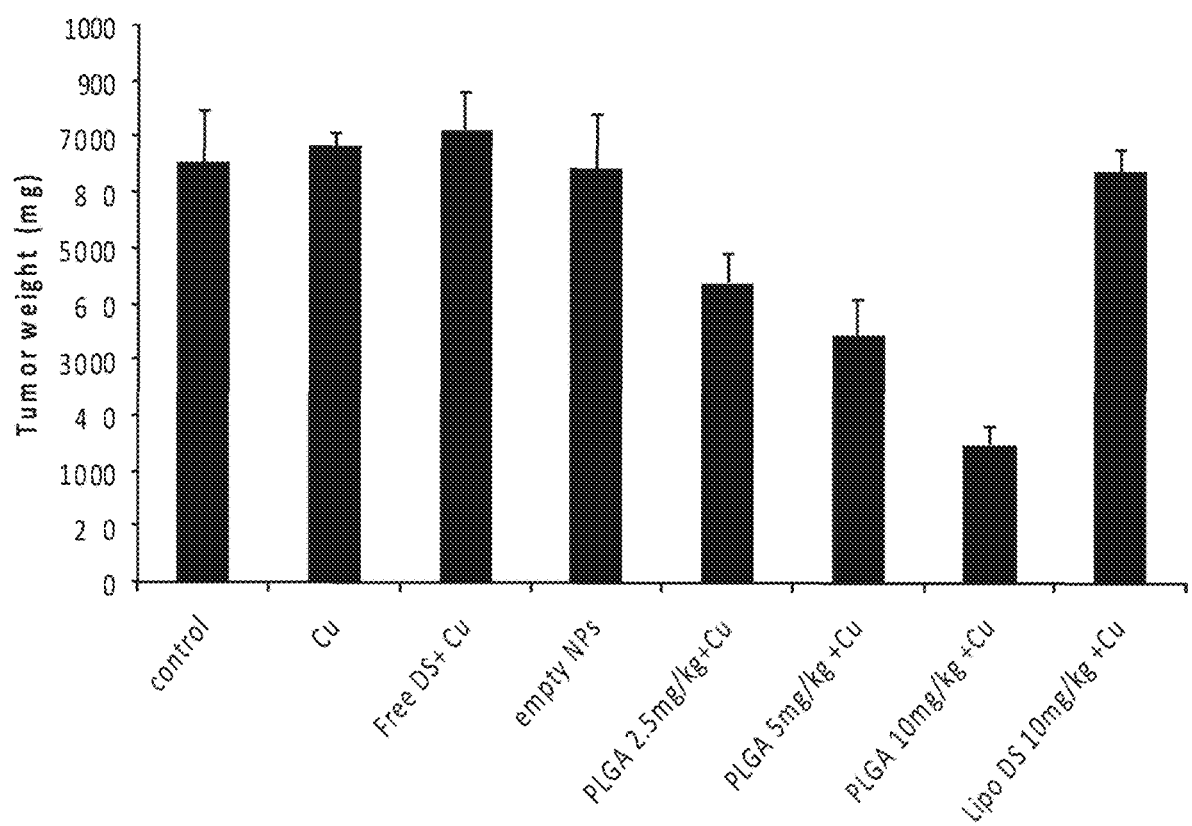
Figure 6C:
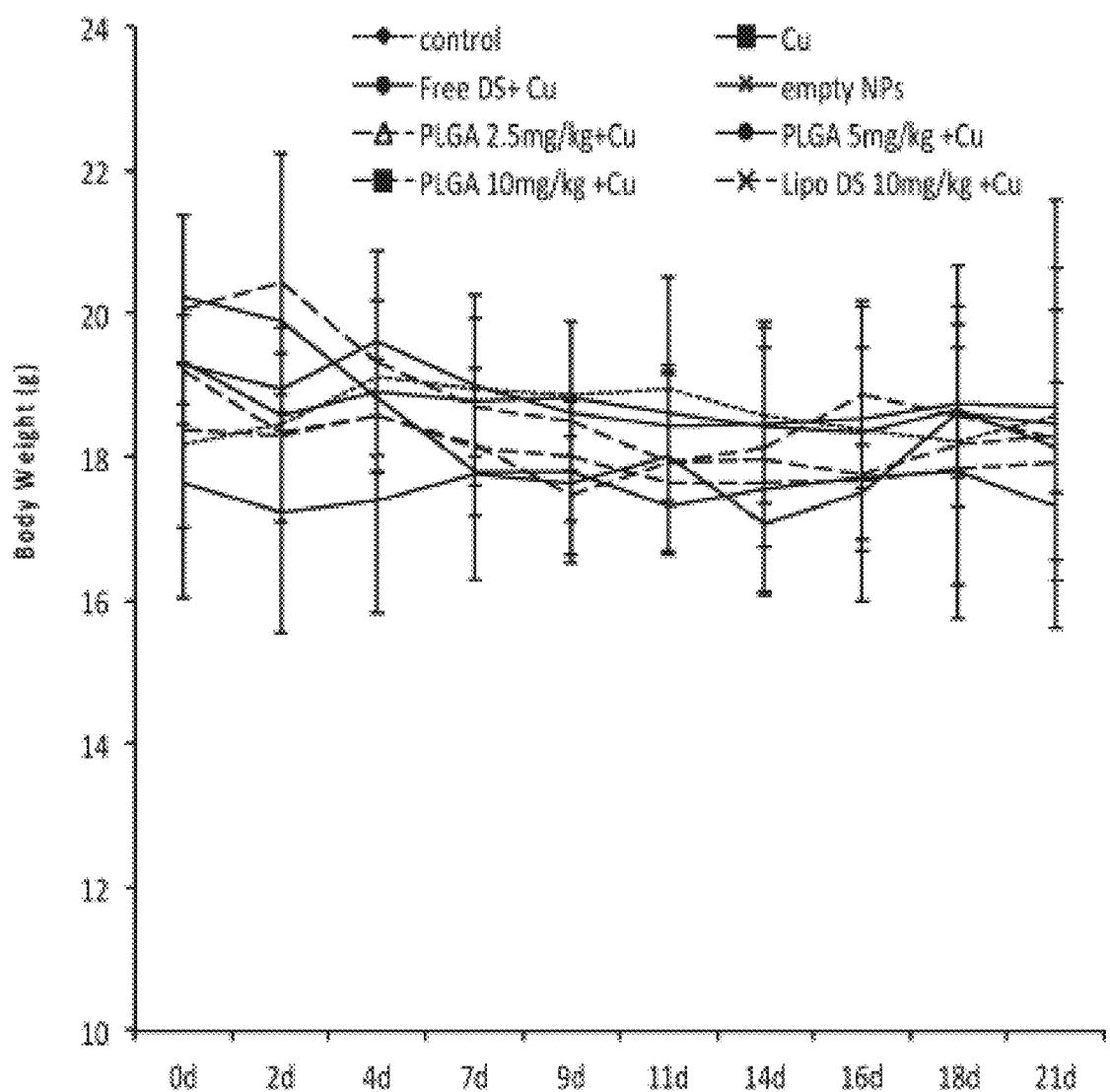

FIG. 6A-C—shows PLGA-disulfiram nanoparticles inhibits growth of xenografts derived from liver cancer cell line. PLC/PRF/5 cells ($5 \times 10^5$) were subcutaneously injected at one front flank of the mice. When the tumor volume reached ~200 $mm^3$, the tumor bearing mice were randomly subdivided into 6 groups (8 mice/group) e.g. control, CuGlu 6 mg/kg p.o., empty nanoparticles+CuGlu 6 mg/kg p.o., PLGA-disulfiram 2.5 mg/kg i.v.+CuGlu 6 mg/kg p.o., PLGA-disulfiram 5 mg/kg i.v.+CuGlu 6 mg/kg p.o., PLGA-disulfiram 10 mg/kg i.v.+CuGlu 6 mg/kg p.o. The drugs were administered 3 times/week for successive 3 weeks.

FIG. 6A—shows xenograft images from different groups. One and 2 xenografts were completely disappeared after 5 mg/kg and 10 mg/kg PLGA-disulfiram treatment, respectively.

FIG. 6B—shows the growth curves of tumor size.

FIG. 6C—shows the weight of tumours at the end of drug treatment.

Figure 7:
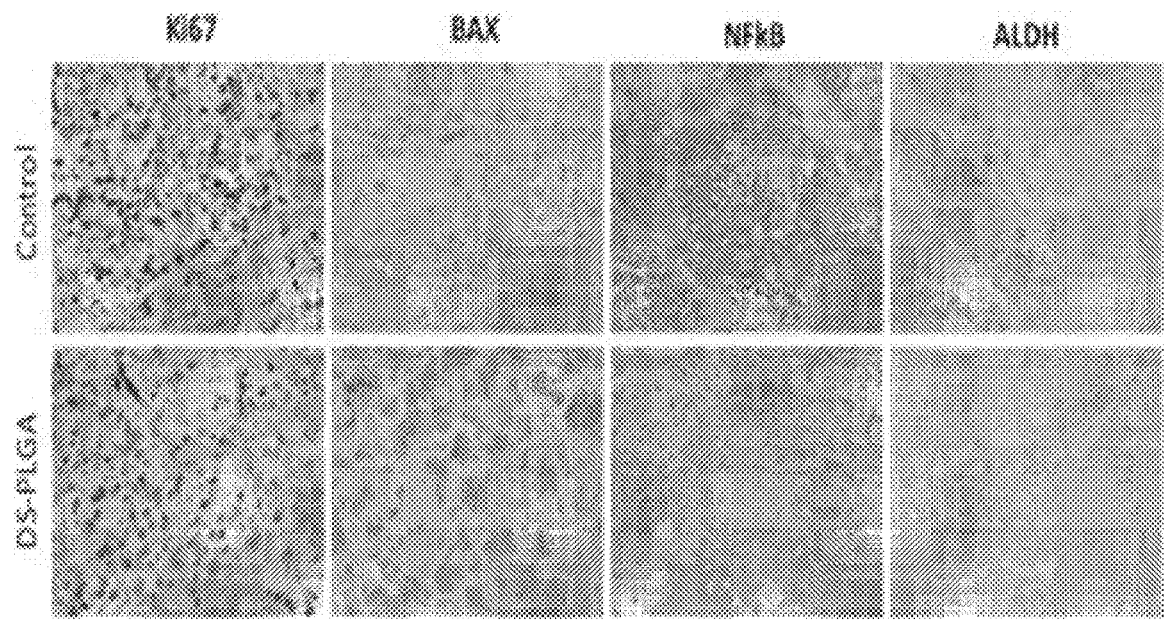

FIG. 7—shows the in vivo effect of PLGA-disulfiram nanoparticles (10 mg/kg) plus Cu Glu (6 mg/kg) on the protein expression of Ki67, BAX, NFκB and ALDH in HCC xenografts (×400 magnification).

Figure 8:
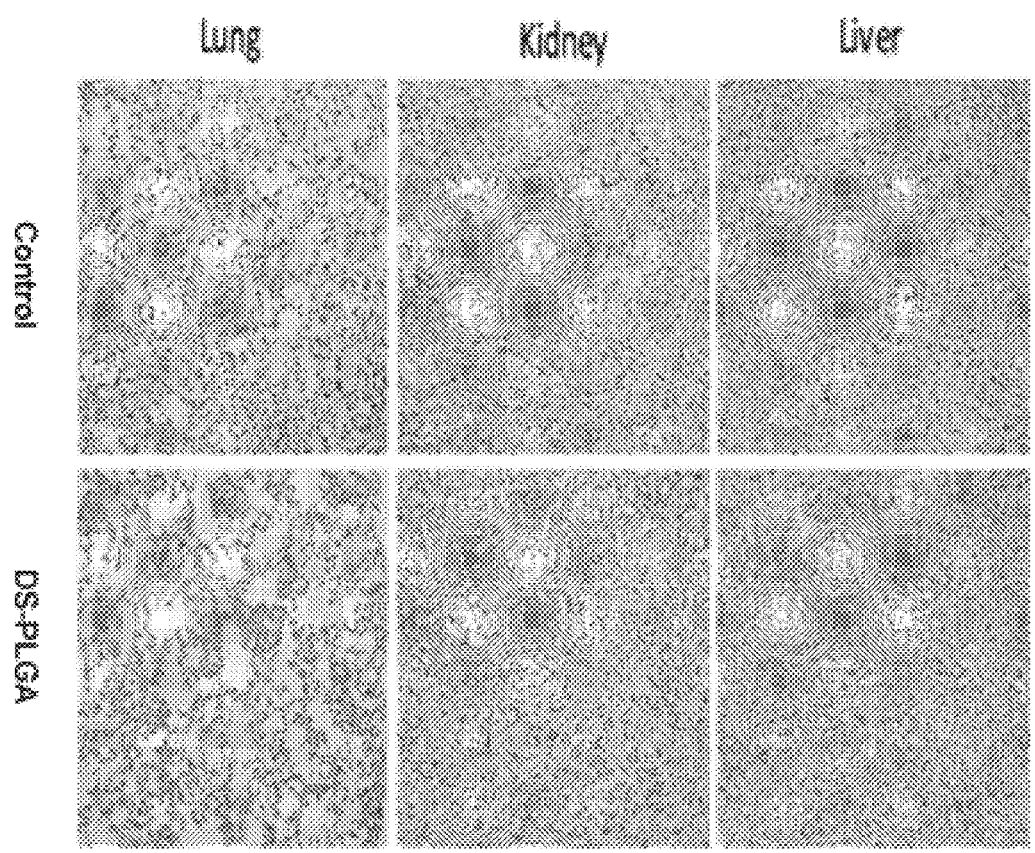

FIG. 8—shows that no toxicity was observed in vital organs in Disulfiram-PLGA nanoparticles and CuGlu treated mice. Representative typical histo-pathological images of lung, liver and kidney in Disulfiram-PLGA nanoparticles plus CuGlu treated mice. (H&E staining, ×400 magnification).

FIG. 9—shows the effect of Disulfiram-PLGA in an intracranial glioblastoma model. BABL/c nude mice (5- to 6-week-old) were anesthetized with an intraperitoneal injection of 0.6 ml of a stock solution containing chloral hydrate (7 µl/g). The surgical site was shaved and prepared with 70% ethyl alcohol and iodine-containing solution. Intracranial injection was performed at the position of parietal midline with a double outer canthus connection intersection 0.5 cm at the right and rear bias. The U87-Luciferase-GFP cells ($2 \times 10^5$ in 5 µl PBS) were delivered using a 25 µl microsyringe drilled to a depth of 0.5 cm. After 10 days, the animals were treated with Disulfiram-PLGA (10 mg/kg iv) plus copper gluconate (6 mg/kg po) three times per week for 4 weeks.

FIG. 9A—shows bioluminescent images.

FIG. 9B—shows brain sections with H&E staining.

FIG. 10—shows the effect of Disulfiram-PLGA on subcutaneous glioblastoma model. U87MG cells ($5 \times 10^6$/mouse) were injected into the front flank of BABL/c nude mice (5- to 6-week-old). After 10 days, the animals were treated with Disulfiram-PLGA (10 mg/kg iv) plus copper gluconate (6 mg/kg po) three times per week for 4 weeks.

Figure 10A:
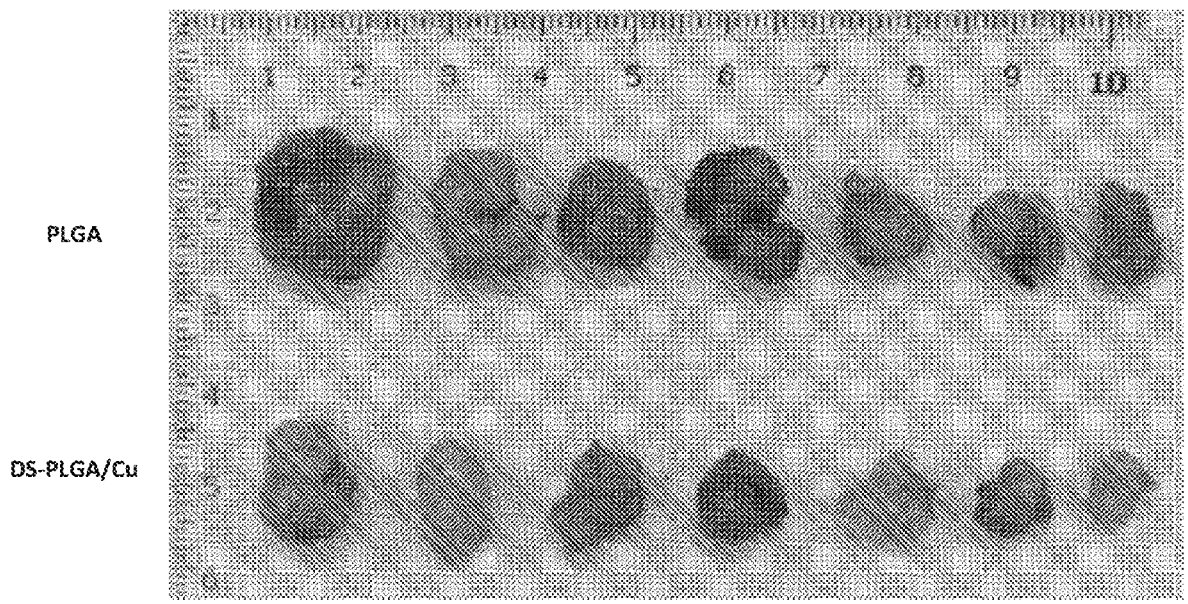

FIG. 10A—shows the morphology of the subcutaneous xenografts.

Figure 10B:
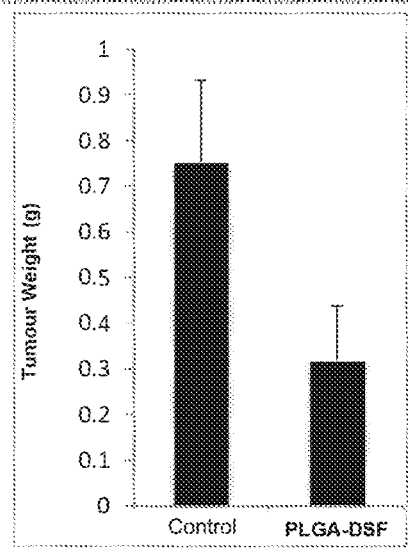

FIG. 10B—shows the tumour weight.

Figure 11:
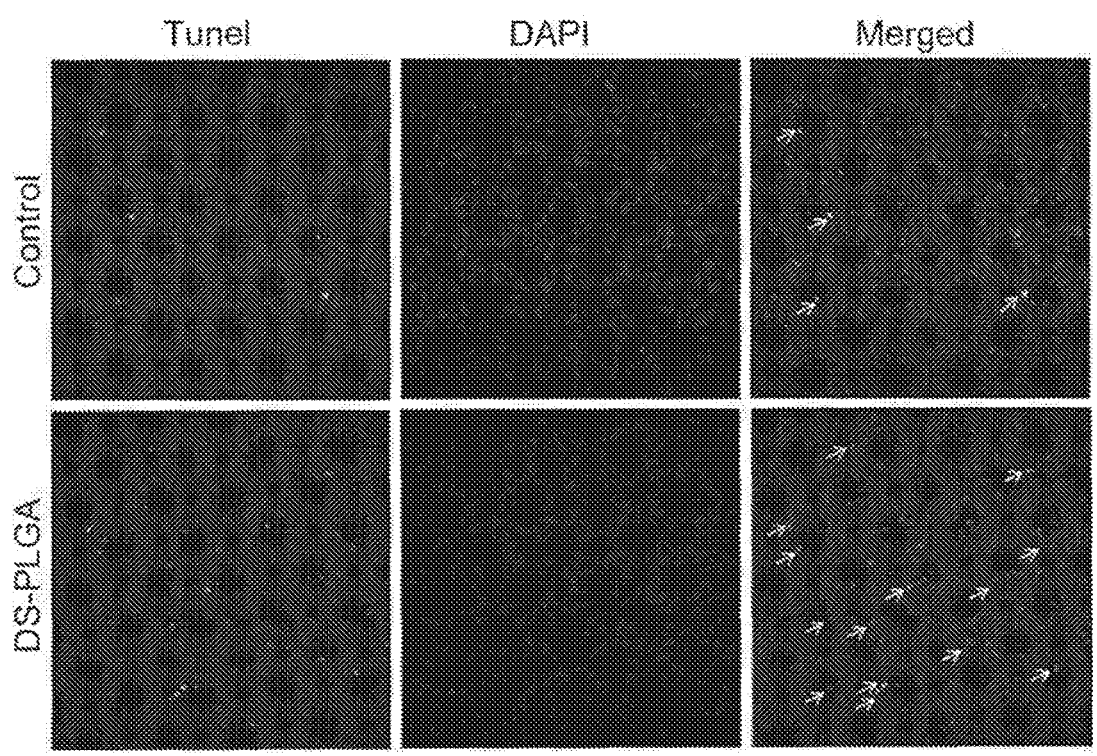

FIG. 11—shows detection of the apoptotic cells in the xenografts by TUNEL staining (arrow heads). (×100 magnification).

Figure 12:
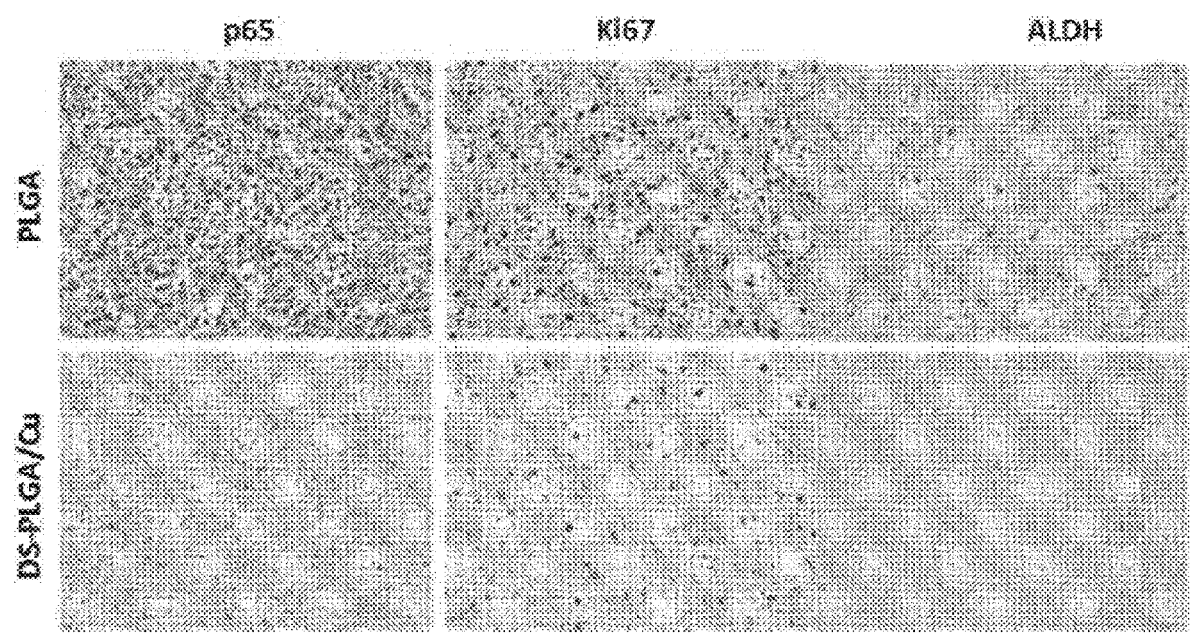

FIG. 12—shows the in vivo effect of PLGA-disulfiram nanoparticles (10 mg/kg) plus Cu Glu (6 mg/kg) on the protein expression of NFκBp65, ki67 and ALDH in glioblastoma xenografts (×400 magnification.

Figure 13:
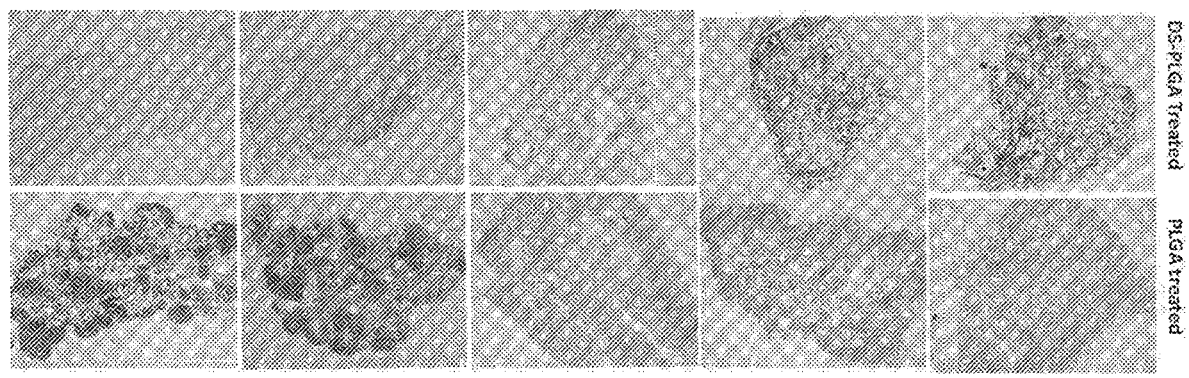

FIG. 13—shows that no toxicity was observed in vital organs in Disulfiram-PLGA nanoparticles and CuGlu treated mice. Representative typical histo-pathological images are shown of lung, liver, spleen, brain and kidney in Disulfiram-PLGA nanoparticles plus CuGlu and PLGA empty nanoparticles treated mice. (H&E staining, ×400 magnification).

Figure 14:
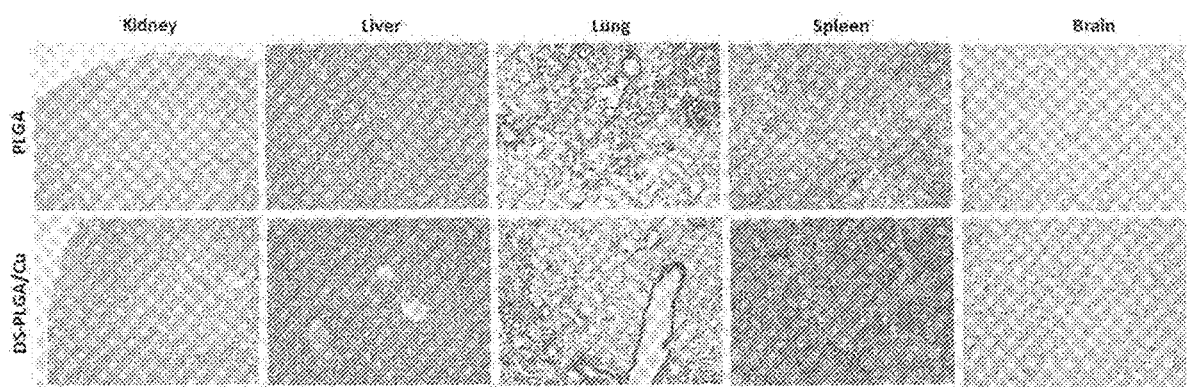

FIG. 14—shows that the tumour occupies most of the lung tissues in the control mice. In contrast, no tumour nodule was detected from the lungs dissected from the treated mice. A549 non-small cell lung cancer (NSCLC) cells ($5 \times 10^6$/mouse) were injected into tail vein. After three days, the mice were treated with disulfiram-PLGA 5 mg/kg, iv+CuGlu 5 mg/kg, po or PLGA empty nano-particles for every other 4 weeks. After 4 months, the mice were sacrificed and the lungs were dissected and sectioned. The slides were H&E stained. The photos were taken at ×20 magnification.

The invention now being generally described, it will be more readily understood by reference to the following examples which are included merely for purposes of illustration of certain aspects and embodiments of the present invention, and are not intended to limit the invention in any way.

Materials and Methods

Materials

The HCC cell lines Huh7 and PLC/PRF/5 were purchased from ATCC (Middlesex, UK). Disulfiram, 5-fluorouracil (5-FU), Sorafenib, copper(II) chloride (CuCl2), copper gluconate (CuGlu), poly lactic-co-glycolic acid (PLGA), Poly (vinyl acetate), cyanomethyl diphenylcarbamodithioate (PVA), dichloromethane were purchased from Sigma (Dorset, UK). DMEM medium and fetal calf serum (FCS) were supplied by Lonza, Wokingham, UK. Ki67 and BAX antibodies were purchased from Cell Signaling. NFkBp65 and ALDH1 antibodies were from AbCam. Sorafenib was purchased from Biovision (CA, USA).

Preparation of Disulfiram-Loaded PLGA Nanoparticles and Nanoparticle Characterization The disulfiram loaded nanoparticles were prepared by an emulsion-solvent evaporation method. PLGA (200 mg) (50: 50 lactide:glycolide) and disulfiram (20, 40, 50, 100 or 150 mg) were dissolved in 10 mL of dichloromethane, and then mixed with 20 mL of 2.5% PVA aqueous solution. This mixture was homogenized for 1 min by vortex and then sonicated using a microtip probe sonicator set at 70% power output (XL 2002 Sonicator® ultrasonic liquid processor) for 3, 4 or 5 min to produce the oil-in-water emulsion. The organic phase was evaporated for 5 h at room temperature. The nanoparticles were recovered by ultracentrifugation (10,000 rpm, 20 min, Hitachi) and then washed twice with water. The purified nanoparticles were freeze-dried in 5% sucrose.

The mean nanoparticle size, distribution and zeta potential of PLGA encapsulated disulfiram nanoparticles were examined. The samples were dispersed in either distilled water or saline (0.154 M and 0.308 M NaCl solution) and measured by dynamic light scattering (DLS) using a Zetasizer (ZS90, Malvern, U.K.) with a scatter angle of 90° at 25° C.

Scanning electron microscopy was performed using a high resolution scanning electron microscope (JEOL JSM T330A). A drop of the nanoparticle samples was mounted on metal stubs and coated with a gold/palladium thin film by sputtering for 60 seconds, with a 15 mA current, using a SPI Module sputter coater system. Images were obtained at an acceleration voltage of 15 kV.

Measurement of the In Vitro Half-Life of Disulfiram

Free disulfiram or disulfiram-PLGA (100 µl at a concentration of 3 mg/ml) was added to an eppendoff tube containing 300 µl of horse serum with shaking at 37° C. The eppendoff tubes were collected and protein was precipitated by the addition of 300 µl of absolute methanol at different time intervals. The supernatant was then subjected to HPLC measurement.

Cumulative Release of Disulfiram-PLGA

The cumulative release profile of disulfiram-PLGA was measured in 0.1 M phosphate buffer solution (PBS, pH 7.4) with 0.5% Tween 80 at 37° C. 10 mg of disulfiram-PLGA was suspended in 25 ml PBS-Tween solution with continual shaking (100 rpm $min^{-1}$) at 37° C. At indicated time intervals, 500 µl of the release media was collected for content measurement by HPLC and an equal volume of fresh media was replenished.

Measurement of Encapsulation Efficiency and Drug Loading Content

The amount of non-entrapped disulfiram was determined by HPLC by UV detection set at 275 nm (SHIMADZU LC-20). The mobile phase was a mixture of methanol:water (70:30%) and the flow rate was set at 1 ml/min. Separation was achieved using a Phenomenex C18 column (250 mm×4.6 mm, 5 µm). The amount of disulfiram entrapped in the nanoparticles was determined after dissolution in dichloromethane. After evaporation of dichloromethane at room temperature, disulfiram was dissolved in pure methanol. The supernatants were passed through a membrane filter (pore size 0.22 µm, Millipore) before being subjected to measurement by HPLC.

Detection of ALDH Activity

The ALDH positive population was detected by ALDEFLUOR kit (StemCell Tech., Durham, N.C., USA) following the supplier's instruction. The cells ($2.5×10^5$) were analyzed after being stained in ALDH substrate containing assay buffer for 30 min at 37° C. The negative control was treated with diethylaminobenzaldehyde (DEAB), a specific ALDH inhibitor. The positively stained population was detected using a FACS Calibur flow cytometer with 488-nm blue laser and a standard FITC 530/30 nm bandpass filter.

Flow Cytometric Analysis of CD133 Expression

The cells ($2.5×10^5$) were incubated with CD133 antibodies (BD Pharmingen, Oxford, UK) for 30 min at 4° C. Unbound antibodies were washed off with 2% FCS HBSS (Sigma) and the cells (10,000 events) were examined no longer than 1 hour post staining on a BD Facscalibur.

Flow Cytometric Detection of Apoptosis

DNA content was used to detect apoptosis of cells. Cells ($1×10^6$) were exposed to empty PLGA nanoparticles plus $CuCl_2$ (5 µM), or PLGA-disulfiram nanoparticles (50 nM) plus $CuCl_2$ (5 µM) for 4 h and harvested by trypsinisation. The cells were fixed in 70% ethanol and then incubated with RNase A (100 µg/ml) and propidium iodide (2.5 mg/ml) for 30 min. The DNA content data from 10,000 cells in each sample was collected by FACS Scan (Becton Dickinson, Franklin Lakes, N.J., USA) and analysed using a CellQuest software (BD Biosciences, Oxford, UK).

In Vitro Cyto-Toxicity of PLGA-Disulfiram to HCC Cell Lines

The PLC/PRF/5 and Huh7 HCC cell lines were cultured in DMEM (Lonza, Wokingham, UK) supplemented with 10% FCS, 50 units/ml penicillin, 50 µg/ml streptomycin. The overnight cultured cells (5,000/well) in 96-well flat-bottomed microtiter plates were exposed to drugs (free disulfiram, PLGA-disulfiram nanoparticles, 5-FU and sorafenib) at indicated concentrations for 72 h in normoxic or hypoxic condition and subjected to a standard MTT assay (Plumb et al., 1989).

Liver Cancer Xenograft Experiments

Five-week-old female BALB/c Nu/Nu athymic nude mice (Biotechology & Cell Biology Shanghai, China) were housed under pathogen-free conditions. PLC/PRF/5 cells ($5×10^5$) were subcutaneously injected at one front flank of the mice. When the tumour volume (V) reached ~200 $mm^3$, the tumour bearing mice were randomly subdivided into 6 groups (8 mice/group) and treated 3 times/week e.g. control; copper gluconate (CuGlu) 6 mg/kg p.o., empty nanoparticles+CuGlu 6 mg/kg p.o., PLGA-disulfiram 2.5 mg/kg i.v.+CuGlu 6 mg/kg p.o.; PLGA-disulfiram 5 mg/kg i.v.+CuGlu 6 mg/kg p.o., PLGA-disulfiram 10 mg/kg i.v.+CuGlu 6 mg/kg p.o. The tumour volume was calculated by the following formula: $V=(L×W^2)×0.5$, where L is the length and W is the width of the tumour. The xenograft size was observed and recorded trice per week for 3 weeks. The animals were sacrificed after three weeks. The tumours and vital organs (lung, liver and kidney) were removed, photographed and subjected to further analysis.

Clonogenic Assay

The overnight cultured cells ($5×10^4$) were exposed to disulfiram (1 µM)/$CuCl_2$ (1 µM) in combination with or without 5-FU (500 µM) or sorafenib (50 µM) for 6 h. The cells were collected and sub-cultured in 6-well plates containing drug-free medium at a cell density of $10^3$/well. After 10 days culture, the clonogenic cells were determined by counting the colonies containing at least 50 cells.

Analysis of the Combinational Effect of 5-FU+Disulfiram-PLGA/Cu and Sorafenib+Disulfiram/Cu by CI-Isobologram Overnight cultured cells were exposed to various concentrations of 5-FU, Sorafenib, disulfiram-PLGA/$Cu_{1\mu M}$ or in combination of 5-FU/disulfiram/$Cu_{1\mu M}$ or Sorafenib/disulfiram/$Cu_{1\mu M}$ at a constant ratio of 5-FU and Sorafenib: Disulfiram=1000:1 and 100:1 respectively. The cells were exposed to disulfiram/Cu for 72 hours and subjected to MTT analysis as described above. The $IC_{50s}$ from single and two-drug-treated cells were detected. The combinational cytotoxicity of 5-FU/disulfiram/$Cu_{1\mu M}$ and Sorafenib/disulfiram/$Cu_{1\mu M}$ was analysed by CI-isobologram analysis using CalcuSyn software (Biosoft, Cambridge, UK)(Chou & Talalay, 1984). The combination index (CI) was determined by mutually exclusive equations.

H&E Staining

Paraffin-embedded sample slides were deparaffinised, hydrated and then stained with hematoxylin for 1 minute. After rinsing, the slides were then stained with eosin for 1 minute, followed by another rinsing step. Coverslips were mounted onto slides with Permount (Fisher Sci, Loughborough, UK).

Immunohistochemistry

The tumor and normal tissues were paraffin embedded. After deparaffinization and rehydration, the slide was blocked its endogenous peroxidase by 3% hydrogen peroxide, incubated with primary antibodies (Ki67, 1:200; BAX, 1:200; NFkBp65, 1:200; ALDH1, 1:200) then with biotinylated secondary antibody, antimouse immunoglobulin G (H+L), followed by incubation in ABC reagent (Avidin and Biotinylated horseradish peroxidase Complex, DAKO Labs, Cambridgeshire, UK). The slide was mounted with 3,3'-diaminobenzidine and visualized under a microscope.

Statistical Analysis

The statistical significance of treatment outcomes was assessed using Student's t-test; $p<0.05$ was considered statistically significant in all analyses.

Results and Discussion

Formulation and Characterization of Disulfiram-PLGA Nanoparticles

Disulfiram-PLGA nanoparticles were prepared by the emulsion solvent diffusion method as described above in the Materials and Methods section. When the feeding ratio of disulfiram and PLGA was 1:2 (w/w), nanoparticles Empty-PLGA and disulfiram-PLGA were prepared with narrow size distribution (131.8±6.9 and 136.2±6.2 nm, respectively (Table 1)) and zeta potential −22.3±0.8 and −21.7±0.96 mV (FIG. 1).

TABLE 1

The effect of sonication time on the nanoparticle size

| | | Sonication time (min) | | |
|---|---|---|---|---|
| | | 3 | 4 | 5 |
| size (nm) | Empty particles | 251.3 ± 11.6 | 131.8 ± 6.9 | 50.1 ± 2.5 |
| | Disulfiram loaded PLGA | 245.7 ± 10.3 | 136.2 ± 6.2 | 49.7 ± 2.9 |

The surface morphology of the nanoparticles was evaluated by performing scanning electron microscopy as described in the Materials and Methods above. The scanning electron microscopy (SEM) image showed that the Disulfiram-PLGA nanoparticles were in analogous spherical shapes (FIG. 1A). Disulfiram-PLGA nanoparticles showed high encapsulated efficiency (78.92±2.16%) with drug loading content (27.67±3.47%).

TABLE 2

The effect of PLGA:Disulfiram ratio on DLC and EE

| Parameters | Formulations | | | | |
|---|---|---|---|---|---|
| PLGA(mg) | 200 | 200 | 200 | 200 | 200 |
| Disulfiram(mg) | 20 | 40 | 50 | 100 | 150 |
| DLC (%) | 9.71 ± 0.24 | 15.83 ± 1.26 | 18.8 ± 1.36 | 27.67 ± 3.47 | 28.71 ± 1.45 |
| EE (%) | 97.31 ± 2.12 | 95.72 ± 2.42 | 94.85 ± 1.92 | 78.92 ± 2.16 | 67.89 ± 3.15 |

DLC: Drug loading content; EE: encapsulation efficiency. The ratio of PLGA:disulfiram at 2:1 was chosen for further experiments.

The stability and release profiles of nanoparticles could markedly affect the drug activity. To determine the effect of serum on disulfiram stability and release, the disulfiram-PLGA nanoparticles were incubated in 1%, 5% and 10% BSA solutions at 37° C. The concentration of disulfiram was examined at different time intervals. The particle size was increased in a time and BSA concentration-dependent manner (FIGS. 1B and C). The zeta potential of the disulfiram-PLGA nanoparticles was also examined after 24 hours incubation in BSA solution. At a physiological concentration of BSA (5%), the disulfiram-PLGA nanoparticles maintained a particle size (162 nm) for at least 8 hours and zeta potential (−15.8 mV) for 24 hours. The disulfiram-PLGA nanoparticles showed very good dispersibility. The cumulative drug release was performed over a period of 7 days in a 0.5% Tween 80 PBS solution (pH 7.4) at 37° C. (FIG. 1D). Results demonstrated a very steady and sustained release of disulfiram from PLGA nanoparticles over 7 days. Approximately 20% of disulfiram was released within 24 hours and reached a 40% release at day 4 which was maintained until the end of the experiment at day 7.

In Vitro Half-Life of Disulfiram

To determine the half-life of disulfiram in vitro, the free disulfiram and disulfiram-PLGA were dispersed into horse serum (100 μg/ml) and incubated at 37° C. The free disulfiram was rapidly degraded in the serum to undetectable levels within 30 seconds (FIG. 1E). In contrast, disulfiram commenced its release from PLGA nanoparticles at 2 min which was equivalent to 34.23±3.38% of the initial drug loading and peaked in 4 min at 51.27±5.98% of the initial drug loading. The controlled release lasted for at least 24 hours. The half-life of disulfiram-PLGA in serum is approximately 6 hours (FIG. 1F). Importantly, after 4 hours incubation, the disulfiram concentration in the serum still remained at ~90 μM which is markedly higher than the $IC_{50s}$ of disulfiram in a wide range of cancer types (~50-500 nM).

In Vitro Cyto-Toxicity of Disulfiram-PLGA Nanoparticles

The cytotoxicity of disulfiram-PLGA was examined in PLC/PRF/5 and Huh7 HCC cell lines using the MTT assay and compared with free disulfiram. $CuCl_2$ (1 μM) was supplemented in all the experiments because it is essential for cytotoxicity of disulfiram [9, 16]. FIG. 2 shows that the in vitro cytotoxic effect of disulfiram-PLGA is comparable to that of the free disulfiram. The $IC_{50s}$ of disulfiram-PLGA and free disulfiram are very similar (p>0.05).

PLGA-Disulfiram Induces Apoptosis in Liver Cancer Cell Lines

The apoptosis in hepatocellular carcinoma cells PLC/R7 and Huh7 cells after incubation of disulfiram-PLGA nanoparticles was investigated. Cells were treated for 4 h. The apoptotic cells (in sub-G1 region in cell cycle) were evaluated by flow cytometry analysis. As shown in FIG. 3, in the control group, the percentage of PLC/R7 or Huh7 cells in the sub-G1 fraction was very low (2.47% or 3.31%), which was indiscernible from those treated with empty nanoparticles and 1 μM $Cu^{2+}$ (2.58% or 3.14%), indicating the biocompatibility of empty PLGA nanoparticles and there was no toxicity of $Cu^{2+}$ at 1 μM on liver cancer cells. However, large populations of the cells (15.68% or 44.47%) went into the sub-G1 phase when treated with 50 nM disulfiram-PLGA and 1 μM $Cu^{2+}$, suggesting disulfiram-PLGA significantly induced apoptosis of liver cancer cells.

Hypoxia-Induced CSC Traits and Conventional Anticancer Drug Chemoresistance in HCC Cell Lines The enhanced ALDH activity and elevated expression of CD133 in hypoxia-cultured PLC/PRF/5 and Huh7 cells indicated that the CSC population was enlarged by a hypoxic environment (FIGS. 4A and B). At hypoxic condition, the HCC cell lines were significantly resistant to 5-FU and Sorafenib (FIGS. 4C and D). CSCs are resistant to conventional anticancer drugs and become the source of tumor recurrence [5]. CSCs reside in a hypoxic/necrotic tumorous area named the CSC niche.

Disulfiram-PLGA Inhibited Expression of CSC Markers and Eradicated Clonogenicity in HCC Cell Lines.

Figure 5A:
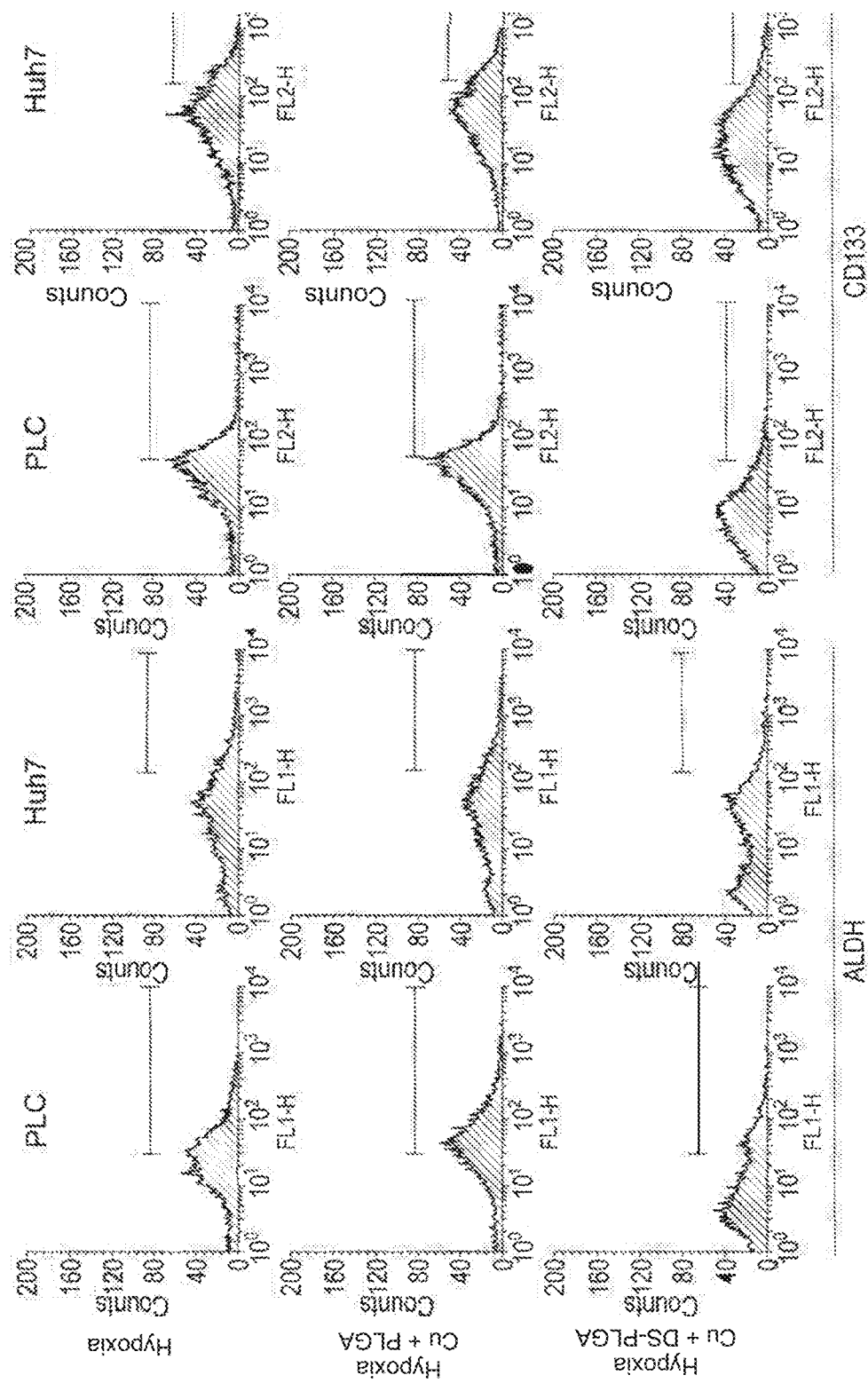
Figure 5B:
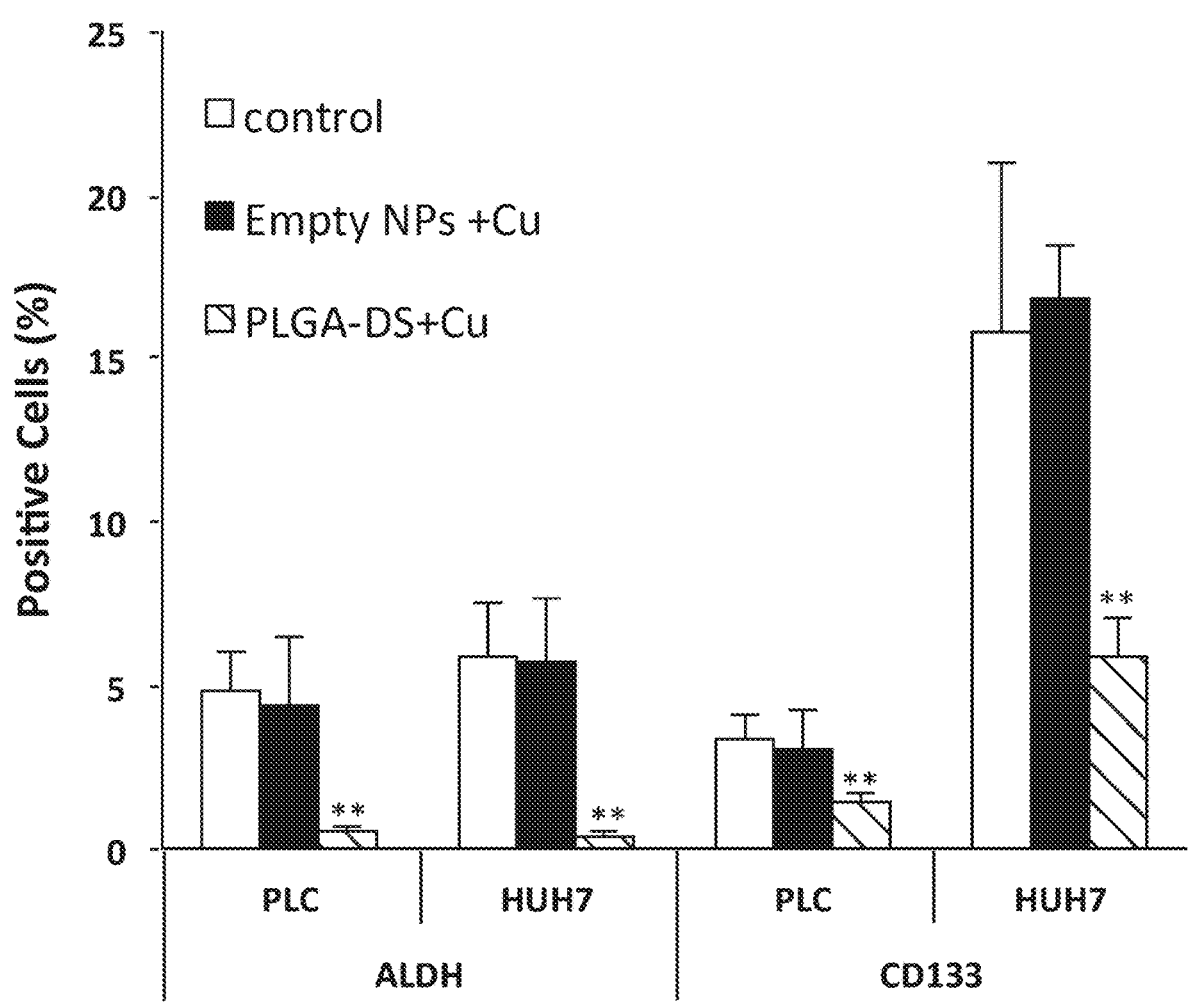
Figure 5C:
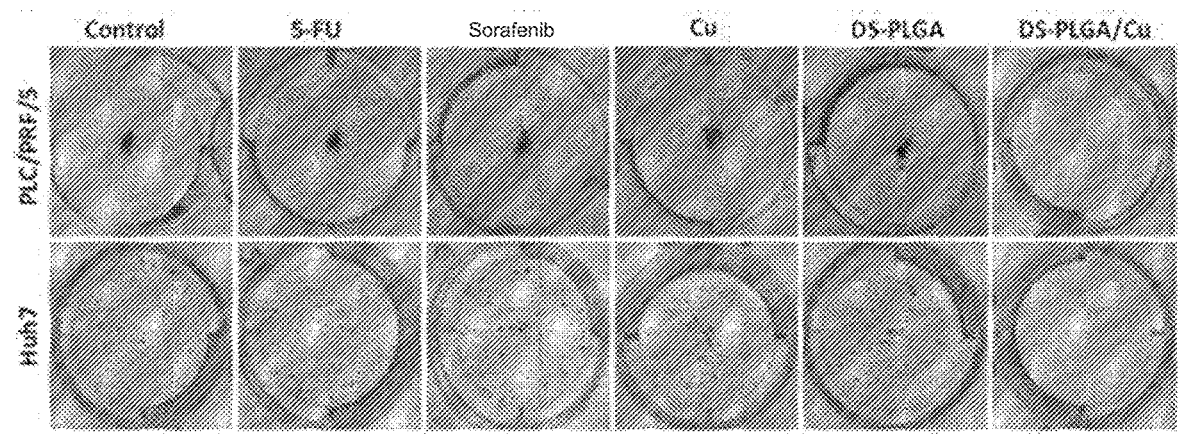
Figure 5D:
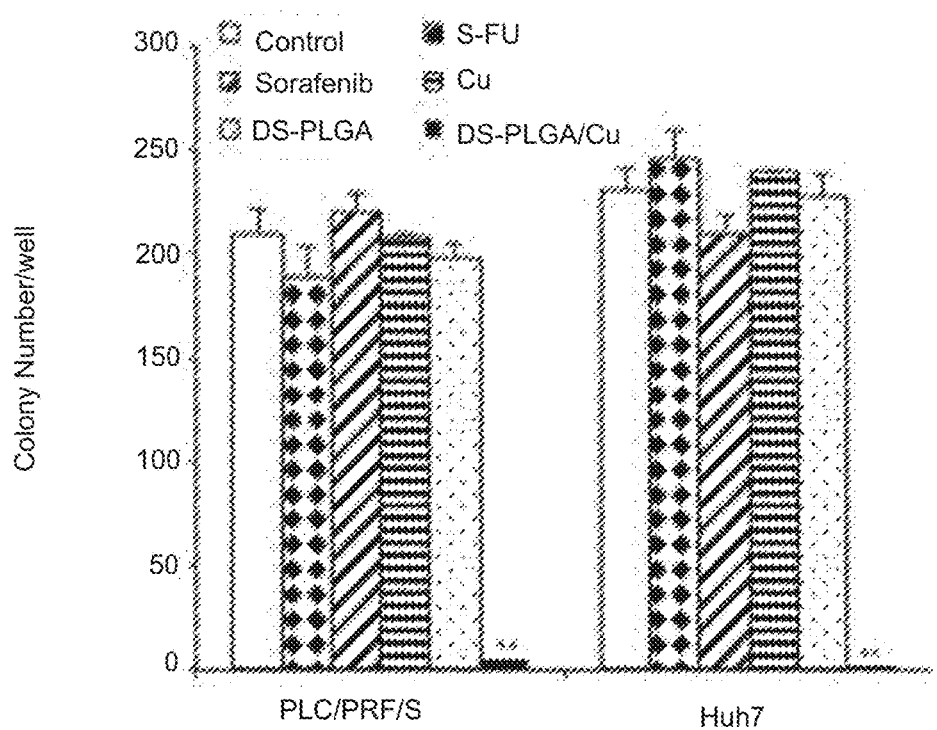

The effect of disulfiram-PLGA on hypoxia-induced CSCs markers in HCC cell lines was examined. Incubation of HCC cells with disulfiram-PLGA at 20 nM with 1 μM $CuCl_2$ for 24 h significantly reduced the $ALDH^+$ and $CD133^+$ cell population in PLC/PRF/5 and Huh7 cell lines (FIGS. 5A and B) suggesting the sufficient inhibitory effect of disulfiram-PLGA on hypoxia-induced CSC population. Clonogenic assays were performed to examine the ability of disulfiram-PLGA/$CuCl_2$ to induce the 'reproductive death' in HCC cell lines. The monolayer-cultured PLC/PRF/5 and Huh7 cells were exposed to 5-FU (200 μM), Sorafenib (20 μM), $CuCl_2$ (1 μM), disulfiram-PLGA (200 nM) or disulfiram-PLGA (200 nM) plus $CuCl_2$ (1 μM) for 6 h. The treated cells were collected and sub-cultured in 6-well plates containing drug-free medium at a cell density of 500 cells/well for another 10 days. In comparison of the control group with the 5-FU, Sorafenib and $CuCl_2$ treated groups, no significant difference in colony numbers was observed (FIGS. 5C and D). In contrast, the colonies in the disulfiram-PLGA/$CuCl_2$ treated group were completely eradicated in both cell lines. Therefore, disulfiram-PLGA/$CuCl_2$ has the ability to eliminate the reproducibility, the typical CSC trait, in the HCC cell lines. Without copper supplement, the colony-forming ability in HCC cell lines was not affected by the exposure of disulfiram-PLGA which indicates that copper is essential for the toxicity of disulfiram-PLGA in HCC stem cells.

The combinational effect of disulfiram-PLGA/Cu and 5-FU or Sorafenib was examined using the CI-isobologram method. Table 3 shows that the cytotoxicity of 5-FU and Sorafenib was significantly enhanced by combination of Disulfiram-PLGA. CI-isobologram indicates very significant synergistic combinational effect between 5-FU, Sorafenib and Disulfiram-PLGA.

TABLE 3

Cytotoxicity of 5-FU, Sorafenib, DS-PLGA, 5-FU/DS-PLGA and Sorafenib/DS-PLGA in HCC cell lines

| | | Huh7 | PLC/PRF/5 |
|---|---|---|---|
| IC50s | | | |
| 5-FU (μM) | | 103.26 (6.21) | 122.84 (8.14) |
| Sorafenib (μM) | | 22.88 (1.26) | 30.89 (2.61) |
| DS-PLGA (nM) | | 30.69 (3.83) | 49.33 (4.11) |
| 5-FU (μM)/DS-PLGA (nM) | | 18.74 (1.09)/ 18.74 (1.09) | 27.56 (1.09)/ 27.56 (1.09) |
| Sorafenib (μM)/DS-PLGA (nM) | | 2.21 (0.19)/ 22.07 (1.88) | 3.08 (0.12)/ 30.77 (1.17) |
| CI Values | | | |
| 5-FU/DS | IC50 | 0.00138 | 0.00298 |
| | IC75 | 0.00106 | 0.00251 |
| | IC90 | 0.00162 | 0.00235 |
| Sorafenib/DS | IC50 | 0.00603 | 0.05093 |
| | IC75 | 0.01007 | 0.09387 |
| | IC90 | 0.01765 | 0.17753 |

The figures are IC50s and CI values, respectively. The numbers in the parentheses are the SD. N = 3. CI values: 0.9-1.1 additive effect; 0.8-0.9 slight synergism; 0.6-0.8 moderate synergism; 0.4-0.6 synergism; 0.2-0.4 strong synergism.

In Vivo Anti-Tumor Activity of Disulfiram-PLGA Nanoparticles

To assess anti-tumor activity in vivo, 2.5 mg/kg, 5 mg/kg and 10 mg/kg disulfiram-PLGA nanoparticles were intravenously injected into the tail veins of the HCC xenograft bearing mice. In comparison with the control group, both 5 mg/kg and 10 mg/kg disulfiram-PLGA significantly inhibited tumor size and tumor weight (FIGS. 6A and B). Copper alone had no effect on tumor growth. The result observed showed that the PLGA encapsulation protected disulfiram from enzymatic degradation in the bloodstream.

The induction of BAX expression in HCC xenografts by disulfiram-PLGA/Cu treatment indicates the in vivo apoptotic effect induced by disulfiram-PLGA/Cu. The inhibition of Ki67 expression in xenograft suggests the anti-proliferation activity of disulfiram-PLGA/Cu treatment. Disulfiram-PLGA/Cu treatment inhibited the expression of NFκB p65 and ALDH in the HCC xenografts (FIG. 7). The disulfiram-PLGA/Cu treatment showed high cancer specificity. No significant body weight difference was observed between the control and treated groups (FIG. 6C). No cytotoxic effect was observed in the vital organs e.g. lung, liver and kidney (FIG. 8).

Anticancer Efficacy of Disulfiram-PLGA in an Intracranial Glioblastoma Model

The anticancer efficacy of disulfiram-PLGA in in situ glioblastoma and non-small cell lung cancer models was investigated. FIG. 9 shows the effect of disulfiram-PLGA on intracranial glioblastoma model. BALB/c nude mice (5- to 6-week-old) were anesthetized with an intraperitoneal injection of 0.6 ml of a stock solution containing chloral hydrate (7 μl/g). The surgical site was shaved and prepared with 70% ethyl alcohol and iodine-containing solution. Intracranial injection was performed at the position of parietal midline with a double outer canthus connection intersection 0.5 cm at the right and rear bias. The U87-Luciferase-GFP cells ($2 \times 10^5$ in 5 μl PBS) were delivered using a 25 μl microsyringe drilled to a depth of 0.5 cm. After 10 days, the animals were treated with disulfiram-PLGA (10 mg/kg iv) plus copper gluconate (6 mg/kg po) three times per week for 4 weeks. Bioluminescent images show that after 4 weeks, all the control mice developed intracranial glioblastoma which infiltrated major part of brain tissue (top panel of FIG. 9A). In contrast, the tumour volumes in the treated group are significantly reduced or disappeared (bottom panel of FIG. 9A). The bioluminescent images were further confirmed by histochemical staining (FIG. 9B).

Anticancer Efficacy of Disulfiram-PLGA in a Subcutaneous Glioblastoma Model

The anticancer efficacy of disulfiram-PLGA in subcutaneous glioblastoma mouse model was examined. U87MG cells ($5 \times 10^6$/mouse) were injected into the front flank of BABL/c nude mice (5- to 6-week-old). After 10 days, the animals were treated with disulfiram-PLGA (10 mg/kg iv) plus copper gluconate (6 mg/kg po) three times per week for 4 weeks. FIG. 10 shows that disulfiram-PLGA treatment also significantly inhibited the subcutaneous tumour growth. FIG. 11 shows that the apoptotic cells in the xenografts were detected by TUNEL staining (arrow heads, ×100 magnification). FIG. 12. shows in vivo that PLGA-disulfiram nanoparticles (10 mg/kg) plus Cu Glu (6 mg/kg) significantly inhibited the protein expression of NFκBp65, ki67 and ALDH in GBM xenografts (×400 magnification).

Anticancer Efficacy of Disulfiram-PLGA in In Situ Non-Small Cell Lung Cancer (NSCLC) Model A549 NSCLC cells ($5 \times 10^6$/mouse) were injected into tail veins of BALB/c nude mice. After three days, the mice were treated with disulfiram-PLGA 5 mg/kg, iv+CuGlu 5 mg/kg, po or PLGA empty nano-particles 2 times/week for every other 4 weeks. The experiment was performed for 4 months. After 4 months, the mice were sacrificed and the lungs were dissected and sectioned. The slides were H&E stained and the photos were taken at ×20 magnification. FIG. 13 shows that the tumour occupies most of the lung tissues in the control mice. In contrast, no tumour nodule was detected from the lungs dissected from the treated mice.

No Toxicity was Observed in Vital Organs in Disulfiram-PLGA Nanoparticles and CuGlu Treated Mice.

FIG. 14 shows the representative typical histo-pathological images of lung, liver, spleen, brain and kidney in Disulfiram-PLGA nanoparticles plus CuGlu and PLGA empty nano-particles treated mice. (H&E staining, ×400 magnification).

Other embodiments are intentionally within the scope of the invention as defined by the appended claims.

The invention claimed is:

1. A nanoparticle consisting of disulfiram or a derivative thereof encapsulated by the copolymer poly(lactic-co-glycolic acid) (PLGA), wherein the PLGA is characterized by a lactic acid:glycolic acid ratio of approximately 50:50, wherein the nanoparticle has a diameter of less than 1000 nm, and wherein the nanoparticle comprises about 4 to about 25 weight percent of the disulfiram or said derivative thereof.

2. A composition comprising more than one said nanoparticle of claim 1.

3. A pharmaceutical composition comprising one or more nanoparticles of claim 1.

4. The nanoparticle of claim 1, wherein the nanoparticle has a diameter of about 100 nm to about 220 nm.

5. The nanoparticle of claim 1, wherein the ratio of PLGA:disulfiram or said derivative thereof is approximately 2:1.

6. The nanoparticle of claim 1, wherein the encapsulation efficiency is between about 68% and about 97%.

7. The composition of claim 2, wherein the nanoparticle has a diameter of about 100 nm to about 220 nm.

8. The composition of claim 2, further comprising a tyrosine kinase inhibitor selected from the group consisting of afatinib, bosutinib, dasatinib, erlotinib, gefitinib, imatinib, nilotinib, pazopanib, ponatinib, regorafenib, semaxinib, sorafenib, sunitinib, telatinib or vandetanib.

9. The composition of claim 8, wherein the tyrosine kinase inhibitor is sorafenib.

10. The composition of claim 2, wherein the ratio of PLGA:disulfiram or said derivative thereof is approximately 2:1.

11. The composition of claim 2, wherein the encapsulation efficiency is between about 68% and about 97%.

12. The pharmaceutical composition of claim 3, wherein the nanoparticle has a diameter of about 100 nm to about 220 nm.

13. The pharmaceutical composition of claim 3, further comprising a tyrosine kinase inhibitor selected from the group consisting of afatinib, bosutinib, dasatinib, erlotinib, gefitinib, imatinib, nilotinib, pazopanib, ponatinib, regorafenib, semaxinib, sorafenib, sunitinib, telatinib or vandetanib.

14. The pharmaceutical composition of claim 13, wherein the tyrosine kinase inhibitor is sorafenib.

15. The pharmaceutical composition of claim 3, wherein the ratio of PLGA:disulfiram or said derivative thereof is approximately 2:1.

16. The pharmaceutical composition of claim 3, wherein the encapsulation efficiency is between about 68% and about 97%.

17. A method of treating cancer, the method comprising administering to a subject in need thereof a therapeutically effective amount of a composition comprising more than one nanoparticle according to claim 1 in combination with a tyrosine kinase inhibitor selected from the group consisting of afatinib, bosutinib, dasatinib, erlotinib, gefitinib, imatinib, nilotinib, pazopanib, ponatinib, regorafenib, semaxinib, sorafenib, sunitinib, telatinib or vandetanib.

18. The method of claim 17, wherein the cancer is liver cancer or brain cancer.

19. The method of claim 17, wherein the composition is a pharmaceutical composition comprising a pharmaceutically acceptable carrier.

20. The method of claim 19, wherein the cancer is liver cancer or brain cancer.

21. The method of claim 17, wherein the nanoparticle comprises about 4 to about 25 weight percent of the disulfiram or said derivative thereof.

22. The method of claim 19, wherein the nanoparticle comprises about 4 to about 25 weight percent of the disulfiram or said derivative thereof.

* * * * *